United States Patent
Cacavas et al.

(10) Patent No.: US 12,366,506 B2
(45) Date of Patent: Jul. 22, 2025

(54) METHOD FOR REMOVING INTERFERING COMPONENTS OF A LIQUID SAMPLE PRIOR TO DISPENSING SAME ON A CHEMICAL REAGENT TEST SLIDE

(71) Applicant: IDEXX Laboratories, Inc., Westbrook, ME (US)

(72) Inventors: Pamela Ann Cacavas, Naples, ME (US); Lucius S. Fox, Gray, ME (US); Robert W. Lachapelle, Leeds, ME (US); Wendy O'Malley LePage, North Yarmouth, ME (US); Evan M. Peck, Gorham, ME (US); Dominic Pelletier, Raymond, ME (US); Eric Allen Steva, Saco, ME (US); Murthy V. S. N. Yerramilli, Falmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 939 days.

(21) Appl. No.: 17/194,713

(22) Filed: Mar. 8, 2021

(65) Prior Publication Data
US 2021/0275979 A1   Sep. 9, 2021

Related U.S. Application Data

(60) Provisional application No. 62/986,988, filed on Mar. 9, 2020.

(51) Int. Cl.
*G01N 1/34* (2006.01)
*B01F 101/23* (2022.01)
*B01L 3/00* (2006.01)

(52) U.S. Cl.
CPC ............. *G01N 1/34* (2013.01); *B01L 3/502* (2013.01); *B01F 2101/23* (2022.01); *B01L 2400/0475* (2013.01)

(58) Field of Classification Search
CPC ......... G01N 1/34; B01L 3/502; B01L 3/5021; B01L 2400/0475; B01L 2200/026; B01F 2101/23; B01F 31/651
See application file for complete search history.

(56) References Cited

U.S. PATENT DOCUMENTS

| 4,389,491 A | 6/1983 | Hanamoto et al. ............. 426/72 |
| 4,644,807 A | 2/1987 | Mar |

(Continued)

FOREIGN PATENT DOCUMENTS

| JP | H07500417 A | 1/1995 | ............. A61M 5/20 |
| JP | H08332315 | 12/1996 | |

(Continued)

OTHER PUBLICATIONS

Simms et al., "Development of zinc chelating resin polymer beads for the removal of cell-free hemoglobin", Jun. 2019, Ann Biomed Eng., 47(6), pp. 1-20. (Year: 2019).*

(Continued)

*Primary Examiner* — Jennifer Weckler
*Assistant Examiner* — Kathryn Elizabeth Limbaugh
(74) *Attorney, Agent, or Firm* — McDonnell Boehnen Hulbert & Berghoff LLP

(57) ABSTRACT

A method using a chemical analyzer for removing a component of a liquid sample which may interfere with a test performed on a test assay includes the steps of adding the liquid sample to a sample cup, transferring a volume of the liquid sample to a mixing cup containing an IMAC (Immobilized Metal Affinity Chromatography) resin containing porous beads to form a sample/resin solution in the mixing cup, using a pipette of the chemical analyzer to repeatedly aspirate the sample/resin solution into a disposable pipette tip of the pipette and expelling the sample/resin solution from the pipette tip into the mixing cup to achieve a mixed (Continued)

sample/resin solution in the mixing cup, and allowing the mixed sample/resin solution in the mixing cup to rest undisturbed so that the interfering component of the liquid sample adheres to the porous beads and the beads settle to a bottom portion of the mixing cup, resulting in a refined liquid sample devoid of the interfering component and occupying an upper portion of the mixing cup for later dispensing on the test assay.

29 Claims, 7 Drawing Sheets

(56) References Cited

U.S. PATENT DOCUMENTS

| | | | |
|---|---|---|---|
| 4,965,187 A | 10/1990 | Tonelli | 435/5 |
| 5,073,344 A | 12/1991 | Smith et al. | 422/69 |
| 5,120,504 A | 6/1992 | Petro | |
| 5,384,248 A * | 1/1995 | Sakata | C12Q 1/28 435/11 |
| 5,869,347 A | 2/1999 | Josef et al. | 436/536 |
| 7,150,973 B2 | 12/2006 | Johnson et al. | 435/7.1 |
| 7,563,410 B2 | 7/2009 | Abele | |
| 7,850,917 B2 | 12/2010 | Ding et al. | |
| 9,116,129 B2 | 8/2015 | Rich et al. | |
| 9,797,916 B2 | 10/2017 | Connolly et al. | |
| 9,823,109 B2 | 11/2017 | Garrepy et al. | |
| 10,335,785 B2 | 7/2019 | Walsh et al. | |
| 10,495,614 B2 | 12/2019 | Pohl et al. | |
| 10,641,768 B2 | 5/2020 | Yoshimura et al. | |
| 10,908,145 B2 | 2/2021 | Sinn Blandy et al. | |
| 11,747,244 B2 | 9/2023 | Glauser et al. | 436/175 |
| 2003/0113316 A1 | 6/2003 | Kaisheva et al. | 424/130.1 |
| 2004/0171169 A1 | 9/2004 | Kallury | |
| 2004/0259162 A1 | 12/2004 | Kappel | |
| 2006/0083659 A1 | 4/2006 | Abele | |
| 2006/0110295 A1 | 5/2006 | Wohleb | |
| 2007/0143063 A1 | 6/2007 | Kaplit | 702/140 |
| 2009/0325263 A1 | 12/2009 | Ponaka et al. | 435/178 |
| 2010/0092980 A1 | 4/2010 | Lee et al. | 435/6.16 |
| 2010/0224012 A1 | 9/2010 | Modic | |
| 2012/0071643 A1 | 3/2012 | Helfer et al. | |
| 2012/0202238 A1 | 8/2012 | Hyde et al. | 435/29 |
| 2013/0017545 A1 | 1/2013 | Yong et al. | |
| 2013/0302384 A1 | 11/2013 | Hiraoka et al. | 424/400 |
| 2014/0288398 A1 | 9/2014 | Simberg et al. | 600/309 |
| 2015/0219636 A1 | 8/2015 | Rychak et al. | 435/5 |
| 2015/0240291 A1 | 8/2015 | Koeda et al. | 435/6.12 |
| 2016/0187306 A1 | 6/2016 | Pohl | |
| 2019/0336916 A1 | 11/2019 | McNeely | |
| 2019/0346348 A1 * | 11/2019 | Glauser | G01N 33/54386 |
| 2020/0398225 A1 | 12/2020 | McNeely | |
| 2022/0016619 A1 | 1/2022 | Sager | |

FOREIGN PATENT DOCUMENTS

| | | | |
|---|---|---|---|
| JP | 2000338014 | 12/2000 | |
| JP | 2004535563 | 11/2004 | |
| JP | 2006119136 | 5/2006 | |
| JP | 2008070346 A | 3/2008 | G01N 33/48 |
| JP | 2015114197 A | 6/2015 | B01D 15/08 |
| JP | 2015159733 A | 9/2015 | C07K 1/04 |
| JP | 2018128394 A | 8/2018 | G01N 30/00 |
| JP | 2019197052 A | 11/2019 | G01N 35/02 |
| WO | WO9303779 A1 | 3/1993 | A61M 5/20 |
| WO | WO2013041556 | 3/2013 | |
| WO | WO2020023899 A1 | 1/2020 | B01D 15/38 |
| WO | WO2020127902 | 6/2020 | |

OTHER PUBLICATIONS

Antoniades et al., "Studies on the State of Insulin in Blood: Materials and Methods for the Estimation of "Free" and "Bound" Insulin-Like Activity in Serum", 1962, Endocrinology, vol. 70, pp. 95-98. (Year: 1962).*

An Office Action, dated Feb. 8, 2024, issued by the Canadian Intellectual Property Office for Applicant's related Canadian Patent Application No. 3,168,170, accorded the international filing date of Mar. 8, 2021.

The Notification of Transmittal of the International Search Report and the Written Opinion of the International Searching Authority, or the Declaration, dated Jul. 23, 2021, which was issued by the International Searching Authority of WIPO in Applicant's corresponding international PCT application having Serial No. PCT/US2021/021331, filed on Mar. 8, 2021.

The Written Opinion of the International Searching Authority, dated Jul. 23, 2021, which was issued by the International Searching Authority of WIPO in Applicant's corresponding international PCT application having Serial No. PCT/US2021/021331, filed on Mar. 8, 2021.

The International Search Report, dated Jul. 23, 2021, which was issued by the International Searching Authority of WIPO in Applicant's corresponding international PCT application having Serial No. PCT/US2021/021331, filed on Mar. 8, 2021.

The Invitation to Pay Additional Fees and, Where Applicable, Protest Fee, dated May 11, 2021, which was issued by the International Bureau of WIPO in Applicant's corresponding international PCT application having Serial No. PCT/US2021/021331, filed on Mar. 8, 2021.

The Notification of Transmittal of the International Search Report and the Written Opinion of the International Searching Authority, or the Declaration, dated May 20, 2021, which was issued by the International Searching Authority of WIPO in Applicant's related international PCT application having Serial No. PCT/US2021/021359, filed on Mar. 8, 2021.

The Written Opinion of the International Searching Authority, dated May 20, 2021, which was issued by the International Searching Authority of WIPO in Applicant's related international PCT application having Serial No. PCT/US2021/021359, filed on Mar. 8, 2021.

The International Search Report, dated May 20, 2021, which was issued by the International Searching Authority of WIPO in Applicant's related international PCT application having Serial No. PCT/US2021/021359, filed on Mar. 8, 2021.

Malynych, et al. "Poly(Vinyl Pyridine) as a Universal Surface Modifier for Immobilization of Nanoparticles", Journal of Physical Chemistry, vol. 106, Issue 6, pp. 1280-1285, Jan. 19, 2002. Abstract available at: https://pubs.acs.org/doi/10.1021/jp013236d (last accessed on Jul. 29, 2021) (full copy of publication enclosed).

A Communication Pursuant to Rule 164(1) EPC, dated Mar. 15, 2024, issued by the European Patent Office in Applicant's related European Patent Application No. EP21768197.2, filed on Mar. 8, 2021.

A Supplementary Partial European Search Report (Mar. 15, 2024— mailed with the Communication Pursuant to Rule 164(1) EPC), issued by the European Patent Office in Applicant's related European Patent Application No. EP21768197.2, filed on Mar. 8, 2021.

A European Search Opinion (Mar. 15, 2024—mailed with the Communication Pursuant to Rule 164(1) EPC), issued by the European Patent Office in Applicant's related European Patent Application No. EP21768197.2, filed on Mar. 8, 2021.

An Office Action (in Japanese) and an English translation thereof, dated Aug. 6, 2024, issued by the Japanese Patent Office for Applicant's related Japanese Patent Application No. 2022-554625, filed on Sep. 8, 2022.

Bio-Works, "Instruction In 40 650 010", full text available at: https://www.ikb-biotech.pl/wp-content/uploads/2017/09/WorkBeads-40-NTA-IDA-pre-charged-with-metal-instructions.pdf (retrieved on Feb. 26, 2025).

Bio-Works, "Work Beads NTA", full text available at: https://www.bio-works.com/product/imac-resin/workbeads-nta (retrieved on Feb. 26, 2025).

Bio-Works, "Data Sheet Ds 40 650 010", full text available at: https://blog.bio-works.com/hubfs/Documents/DS-40-650-010-AA-WorkBeads-Charged-40-NTA-and-40-IDA.pdf?hsLang=en.

(56) References Cited

OTHER PUBLICATIONS

DaNa, "Cross Cutting", full text available at: https://nanopartikel.info/en/basics/cross-cutting/.

Loos, et al., Functionalized polystyrene nanopartilces as a platform for studying bionano interactions, Beilstein Journal of Nanotechnol., vol. 5:2403-2412 (2014).

Arrubeo, et al., "Antibody-Conjugated Nanoparticles for Biomedical Application", Journal of Nanomaterials, VOI 2009, Article ID 439389, pp. 1-24 (2009).

Simms, et al., "Development of zinc chelating resin polymer beads for the removal of cell-free hemoglobin", Annals of Biomedical Engineering, 47:1470-1478 (2019).

Antoinades, et al., "Studies on the State of Insulin in Blood: Materials and Methods for the Estimation of "Free" and "Bound" Insulin-Like Activity in Serum", Endocrinology, 70:95-98 (1962).

Porex Filtration Group, "Porous Polymers Technologies", full text available at: https://www.porex.com/porous-polymers-technology/.

GE Osmonics, "Osmonics MAGNA Nylong Transfer membrante", full text avialable at: https://www.krackeler.com/catalog/product/3751/Osmonics-MAGNA-Nylon-Transfer-Membrane.

Milliporesigma, "Durapore Membrane Filter", full text available at: https://www.emdmillpore.com/US/en/product/Durapore-Memprane LFilters, MM_NF-C7631#overview.

Celanese, "Binders for Glass Fiber Chopped Strand Mat Production", full text available at: https://ww.celanese.com/emulsion-polymers/product-groups/Glass-filber-0CSM-polymers-europe.aspx (retrieved on Feb. 26, 2025).

* cited by examiner

METHOD FOR REMOVING INTERFERING COMPONENTS OF A LIQUID SAMPLE PRIOR TO DISPENSING SAME ON A CHEMICAL REAGENT TEST SLIDE

CROSS-REFERENCE TO RELATED APPLICATIONS

This application is related to U.S. Provisional Patent Application Ser. No. 62/986,988, filed on Mar. 9, 2020, and titled "Method For Removing Interfering Components Of A Liquid Sample Prior To Dispensing Same On A Chemical Reagent Test Slide", the disclosure of which is hereby incorporated by reference and on which priority is hereby claimed.

This application is also related to U.S. Provisional Patent Application Ser. No. 62/987,077, filed on Mar. 9, 2020, and titled "Matrix And Associated Sample Or Mixing Cup Used For Removing Components Of A Liquid Sample", naming IDEXX Laboratories, Inc. as the applicant, the disclosure of which is incorporated herein by reference.

BACKGROUND OF THE INVENTION

Field of the Invention

The present invention generally relates to techniques for dispensing liquid samples on dry chemistry test slides, and more particularly relates to methods for removing impurities from the liquid sample. Even more specifically, the present invention relates to a method of purifying a liquid sample to remove components thereof which could affect the accuracy of fluorescence or absorbance/reflectance measurements taken by an automated chemical analyzer on the liquid sample.

Description of the Problem to be Solved

Certain assays used in dry chemistry and wet chemistry analysis techniques may be susceptible to interfering components of a liquid sample when fluorescence or absorbance/reflectance tests are performed on the liquid sample. As an example, bile acid dry chemistry test slides are highly sensitive to hemoglobin interference primarily due to the interaction of hemoglobin with tetrazolium dye on the slides. In this regard, reference should be had to FIG. 1 of the drawings, which is a graph of actual reflective density (ordinate) versus time (abscissa) in seconds of bile acid assays for five undiluted blood samples having different concentrations of hemoglobin (Hgb) in milligrams (mg) per deciliter (dL). The graph of FIG. 1 shows the impact on instrument progress curves from samples containing progressively increasing concentrations of hemoglobin and how such hemoglobin concentrations interfere with bile acid reflective density measurements. Such interference is caused by hemolysis of the blood sample. The samples are deposited on the test slides at time=0 in FIG. 1. The curves overlap at time≤0 in FIG. 1, which indicates a baseline measurement of about 0.075 in reflective density, representing successive reads of unspotted slides before the samples have been dispensed. The curve labeled N in the graph of FIG. 1 represents the hypothetical bile acid reflective density measurement if no interference caused by hemolysis of the blood sample occurred (i.e., Hgb=0 mg/dL). Many, if not most, commercially available bile acid assays are susceptible to hemoglobin interference.

One way envisioned to overcome this problem is to devise a bile acid assay formulation, whether using dry or wet chemistry, which is not, or is only minimally, affected by the presence of hemoglobin in the liquid sample. To the knowledge of the inventors herein, such an assay is not currently available and would require extensive time and expense to develop. Another path to solving the problem of hemolysis interference in bile acid measurements, which is the avenue taken by the inventors and described herein, is to decrease hemoglobin levels in the sample prior to tests being performed, and using existing, currently available, bile acid assays.

OBJECTS AND SUMMARY OF THE INVENTION

It is an object of the present invention to provide a method for removing interfering components of a liquid sample prior to the sample being dispensed on a dry chemistry reagent test slide.

It is another object of the present invention to provide a method for removing components of a liquid sample that may interfere with diagnostic measurements performed on the liquid sample.

It is still another object of the present invention to provide a method for removing impurities from a liquid sample using functionalized particles prior to the sample being tested.

It is a further object of the present invention to provide a method for removing hemoglobin or other constituents of a liquid sample that may affect the accuracy of tests performed on the liquid sample.

It is yet a further object of the present invention to provide a liquid sample mixing/dispensing technique that removes components of the sample that may interfere with tests performed on the liquid sample and measurements derived therefrom.

It is yet another object of the present invention to provide a pretreated liquid sample having a minimized or negligible concentration of hemoglobin therein prior to the pretreated liquid sample being dispensed on a bile acid dry chemistry reagent test slide.

It is still a further object of the present invention to use a currently available, automated chemical analyzer for analyzing reagent test slides to condition the liquid sample such that the sample has a reduced concentration of an interfering component which may have otherwise affected the accuracy of fluorescence or absorbance/reflectance measurements derived from tests performed on the liquid sample.

It is another object of the present invention to provide a method for removing interfering components of a liquid sample using a conventional chemical analyzer and dispensing the liquid sample on a conventional, unmodified, dry chemistry reagent test slide.

It is still another object of the present invention to provide a method of pre-conditioning a liquid sample by removing or minimizing the presence of an interfering component thereof prior to dispensing the same on a conventional reagent test slide, the method thereby advantageously avoiding the time and expense of developing a test slide assay that is not sensitive to the interfering component.

In accordance with one form of the present invention, a liquid sample is prepared for testing by removing components thereof which may interfere with tests performed on the sample. Such interfering components are removed by advantageously using a conventional, currently available, automated chemical analyzer having pipetting capabilities.

Also, advantageously, the pre-conditioned liquid sample, with the interfering components removed therefrom, may now be tested using an off-the-shelf test assay, such as a dry chemistry reagent test slide. The test slide used for conducting measurements on the liquid sample may still be sensitive to the interfering component of the liquid sample, but since such a component has been substantially removed from the sample, the slide assay need not be modified to render it insensitive to the component.

In a preferred form of the present invention, the interfering component is removed from the liquid sample, or its concentration therein is at least minimized, by mixing functionalized particles with the liquid sample in a mixing cup prior to the sample being dispensed on the assay for testing. Such functionalized particles may be in the form of agarose-based porous beads, as one example, to which the interfering component in the liquid sample adheres and is removed from solution as particles settle through the action of gravity (although light centrifugation is also envisioned to be used to accelerate particle settling). Mixing of the functionalized particles and the liquid sample may be performed using a dispensing/aspirating pipette of a conventional chemical analyzer.

Once the functionalized particles and liquid sample are fully mixed in the mixing cup, the mixture is allowed to rest undisturbed for a first predetermined period of time to allow the particles, with the interfering component of the liquid sample adhered thereto, to settle to the lower portion of the mixing cup by gravity, for example. Then, the pipette of the chemical analyzer aspirates into the pipette tip a predetermined volume of liquid sample from the upper portion of the mixing cup. The liquid sample in the upper portion of the mixing cup should be free, or have a reduced concentration, of the interfering component.

As a precaution, and as an optional step in the method, the volume of liquid sample aspirated into the pipette tip may further be allowed to rest undisturbed for a second predetermined period of time so that any remaining functionalized particles, with or without the interfering component adhering thereto, aspirated into the pipette tip will settle by gravity to the bottom section of the pipette tip. After this predetermined second period of time has elapsed, a volume of liquid containing settled-out particles and/or interfering sample component occupying the bottom section of the pipette tip is expelled or "spit out" from the pipette tip into the mixing cup. The volume of liquid sample remaining in the pipette tip, or a portion thereof, which should be substantially free or have a lower concentration of the interfering component of the liquid sample, may now be dispensed by the pipette of the chemical analyzer onto a chemical reagent test slide.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

Reference should now be had to FIGS. 2, 3, 4A, 4B and 5-7 of the drawings. As described previously, certain assays may be sensitive to components of a liquid sample which may interfere with tests performed on the liquid sample and which may affect the accuracy of any measurements taken. For example, bile acid tests are performed on a subject, human or animal, if liver malfunction is suspected. In the case of animals, a preprandial blood sample is drawn, and after a predetermined time has elapsed after the animal has eaten, a postprandial blood sample is collected. Both samples are provided to a laboratory and tested for bile acid levels either using wet chemistry assays or dry chemistry reagent test slides.

Figure 1:
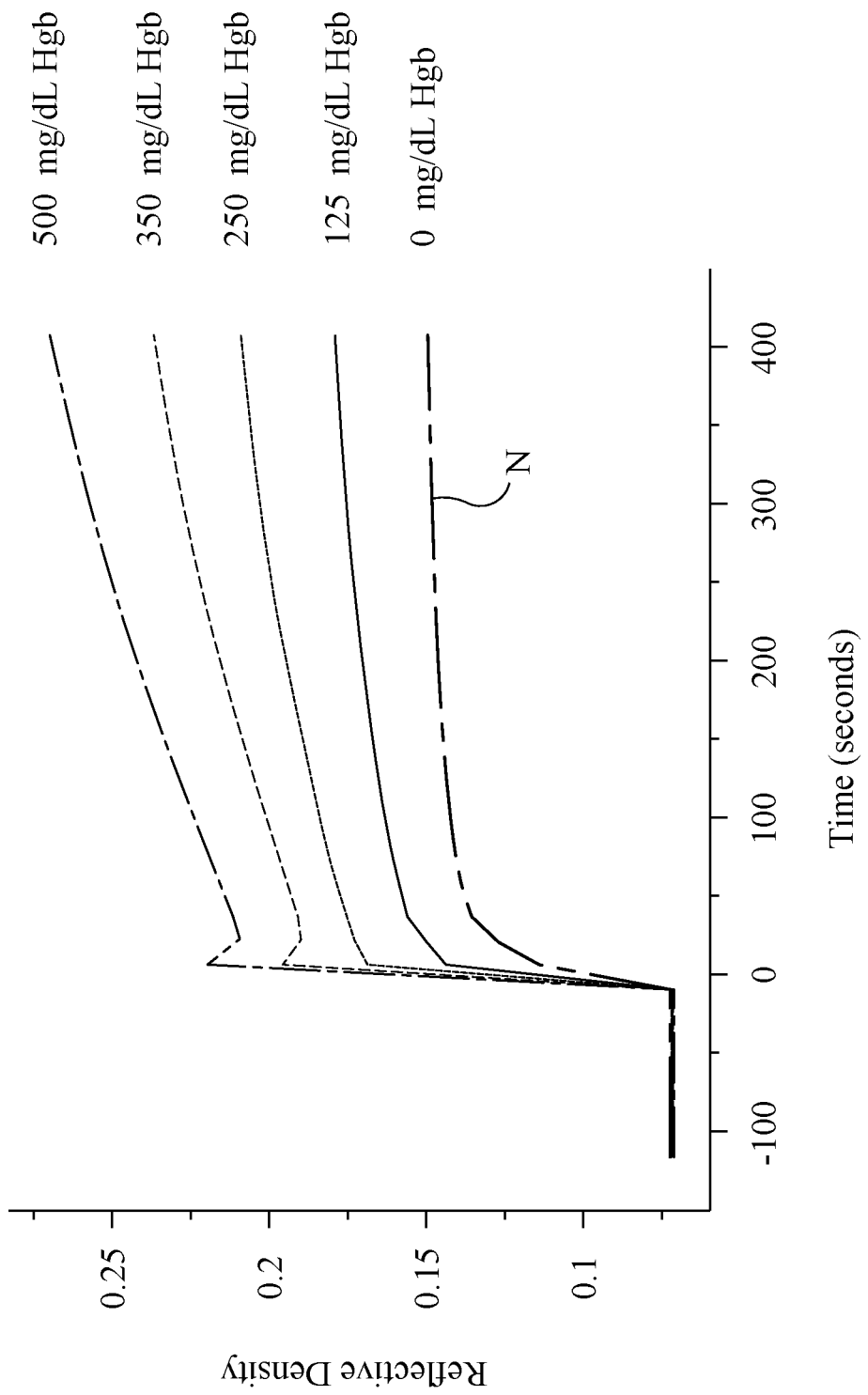
FIG. 1 is a graph of measurements of actual reflective density (ordinate) versus time in seconds (abscissa) for a sample of undiluted blood plasma having five different concentrations of hemoglobin (Hgb) in milligrams (mg) per deciliter (dL).

The problem with such bile acid assays is that they are sensitive to hemoglobin (Hgb), which interferes with the bile acid tests performed on the patient's blood sample and may render any measurements taken inaccurate, as exemplified in the graphs provided in FIG. 1 and discussed previously. So, the choices in solving this problem are either developing a bile acid assay which is insensitive to hemoglobin in the blood sample, which may be an expensive and time consuming avenue to take, or providing a method for substantially removing the interfering component, in this case, hemoglobin, or at least minimizing the concentration thereof, in the blood sample prior to the sample being dispensed on the assay for testing. This latter approach is what has been taken by the inventors and is described more fully herein. It should be realized, of course, that the method of the present invention described herein may be used to reduce the concentration of an interfering component of a liquid sample to which a test assay may be sensitive, and should not be construed as being limited to a method for removing hemoglobin from a blood sample prior to the sample being dispensed on a test assay. In fact, the method of the present invention may be used to remove, or reduce the concentration of, other components of a liquid sample, including proteins.

In accordance with one form of the present invention, in which, by way of example only, bile acid test slides that are sensitive to hemoglobin in the blood sample are used and tested in an automated chemical analyzer having sample aspirating/dispensing capabilities using a pipette fitted with a disposable tip, functionalized particles are pre-mixed in a mixing cup holding the blood sample ("blood sample" used herein generally refers to whole blood, diluted blood, plasma, serum, or the like). These functionalized particles cause the interfering component of the blood sample, in this example, hemoglobin, to adhere to the particles and, together, the particles and hemoglobin adhering thereto will settle to the lower portion of the mixing cup by gravity.

Preferably, the functionalized particles envisioned to be used to remove hemoglobin from the blood sample are agarose-based porous beads. Such particles are used in Immobilized Metal Affinity Chromatography (IMAC) applications that are functionalized by attaching ligands that are subsequently coordinated to metal ions. To remove hemoglobin from the blood sample for bile acid tests, the preferred particles have a chelating ligand based on nitrilotriacetic acid (NTA) or, alternatively, iminodiacetic acid (IDA), and Nickel ions ($Ni^{2+}$) or, alternatively, cobalt ($Co^{2+}$) or zinc ($Zn^{2+}$) ions. The porous beads in resin form are preferably purchased from Bio-Works Technologies AB located in Uppsala, Sweden as Part No. 40 651 001 (for an NTA with Ni-2), and reference should be had to Bio-Works Data Sheet DS 40 650 010 for more information on such porous beads and resins, the disclosure of which is incorporated herein by reference.

More specifically, the types of resins manufactured by Bio-Works Technologies AB which are suitable for use in the method of the present invention are cross-linked agarose resins that contain either of two chelating groups, NTA or IDA, as mentioned previously, charged with one of four metal ions (nickel, cobalt, zinc and possibly copper (Cu)). Preferably, the resins are packaged in water, with a preservative, prior to their use, or the resins may be packaged in ethanol. The following part numbers of resins from Bio-Works Technologies AB may be suitable for use: 40 651 001 (Ni-NTA); 40 651 003 (Ni-NTA); 40 651 010 (Ni-NTA); 40 651 401 (Co-NTA); 40 651 403 (Co-NTA); 40 651 410 (Co-NTA); 40 651 301 (Cu-NTA); 40 651 303 (Cu-NTA); 40 651 310 (Cu-NTA); 40 651 501 (Zn-NTA); 40 651 503 (Zn-NTA); 40 651 510 (Zn-NTA); 40 650 001 (Ni-IDA); 40 650 003 (Ni-IDA); 40 650 010 (Ni-IDA); 40 650 401 (Co-IDA); 40 650 403 (Co-IDA); 40 650 410 (Co-IDA); 40 650 301 (Cu-IDA); 40 650 303 (Cu-IDA); 40 650 310 (Cu-IDA); 40 650 501 (Zn-IDA); 40 650 503 (Zn-IDA); and 40 650 510 (Zn-IDA). It is also envisioned to be within the scope of the present invention to use a bead resin forming a component of a buffer solution or diluent that is added to a liquid sample.

Furthermore, resins containing porous beads or non-porous beads may be used in accordance with the method of the present invention. For example, gels containing non-porous silica beads may be used. Suitable silica-based gels include, but are not limited to, those commonly known as "scavenger resins" manufactured by SiliCycle Inc. of Quebec City, Quebec, Canada and further referred to as Imidazole-silica, AMPA silica, DOTA silica, DMT silica and TAAcOH silica, and also mesoporous thiol-silica manufactured by Sigma-Aldrich, Inc., now MilliporeSigma, owned by Merck KGaA of Darmstadt, Germany. Other materials which may be suitable for use in removing an interfering component of a blood sample, and in particular, hemoglobin, include the IMAC resins mentioned previously, including the NTA-Ni (and other metals, such as Zn, Al, Mn, Co and others) resins, TALON™ resins (EDTA), such as those manufactured by Takara Bio USA, Inc. of Mountain View, California, and Iminodiacetate-Ni resins; and other materials, including Fractogel®-Ni activated products manufactured by Merck KGaA of Darmstadt, Germany, TCEP immobilized resin products, ConA resin products and protein depletion resins, each of which is manufactured by Thermo Fisher Scientific Inc. of Waltham, Massachusetts.

Immobilized Metal Affinity Chromatography (IMAC for short) is a common technique used in the purification of recombinant proteins tagged with histidine or polyhistidine. The IMAC resin, containing agarose-based porous beads, is added to the consumable (discardable) mixing cup as a sample treatment mitigation for hemolysis interference in the bile acid assay, that is, as a way to remove or reduce the quantity of hemoglobin in the blood sample prior to the sample being metered onto the bile acid test slide, as hemoglobin in the sample is bound by immobilized metal ions in the IMAC resin.

Figure 2:
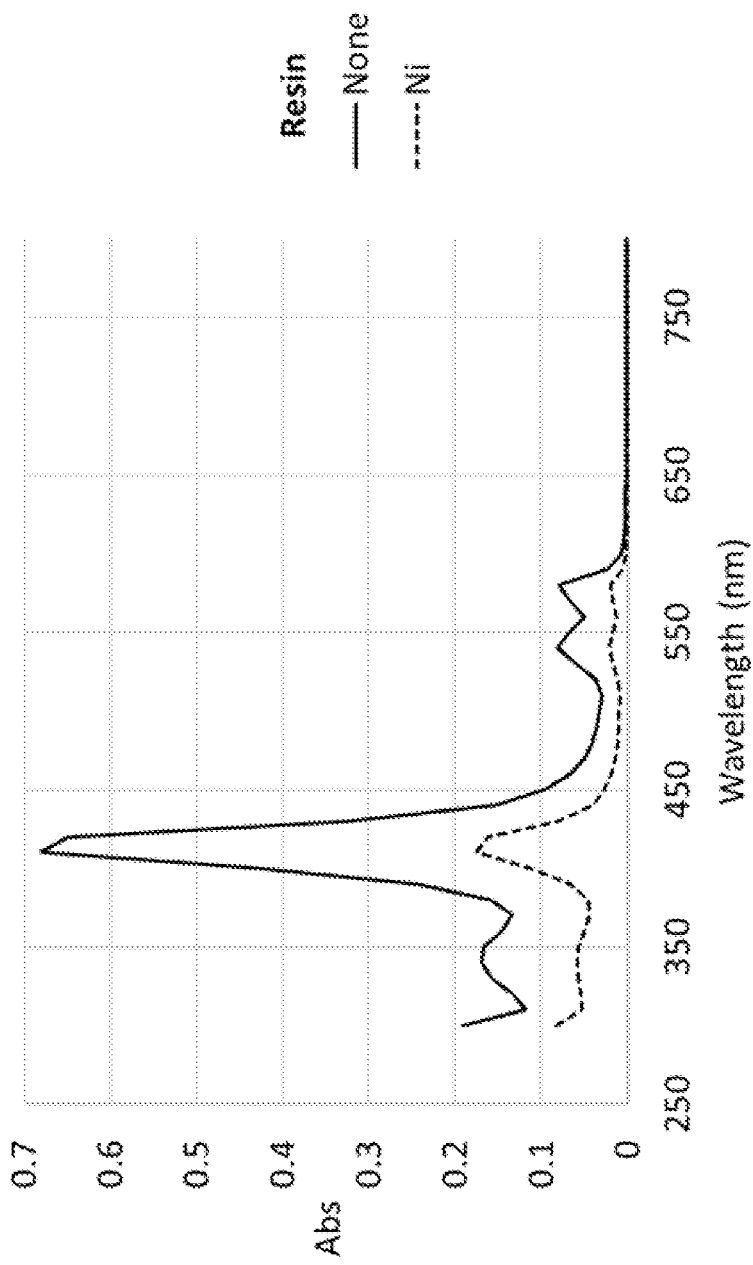
FIG. 2 is a graph of absorption (ordinate) versus wavelength in nanometers (abscissa) of 500 mg/dL hemoglobin (Hgb) in a canine plasma sample with no treatment compared to treatment with a Ni IMAC (Immobilized Metal Affinity Chromatography) resin (33% resin, 66% sample), in accordance with the method of the present invention, and illustrating how hemoglobin has been reduced from about 500 mg/dL to about 100 mg/dL using the IMAC resin treatment of the present invention to remove hemoglobin from the sample.

FIG. 2 illustrates the efficacy of the method of the present invention, which will be described in greater detail hereinafter. As can be seen in the graph depicted in FIG. 2, the absorption spectra of hemoglobin content of a canine plasma sample with no IMAC treatment has been overlaid on the absorption spectra of the same sample having undergone IMAC treatment in accordance with the method of the present invention. It is evident from the graph that there is a five-fold reduction in the hemoglobin content in the sample using this treatment protocol; that is, hemoglobin (Hgb) has been reduced in the exemplary sample from about 500 mg/dL to about 100 mg/dL after the blood sample underwent IMAC treatment in accordance with the method of the present invention.

Figure 3:
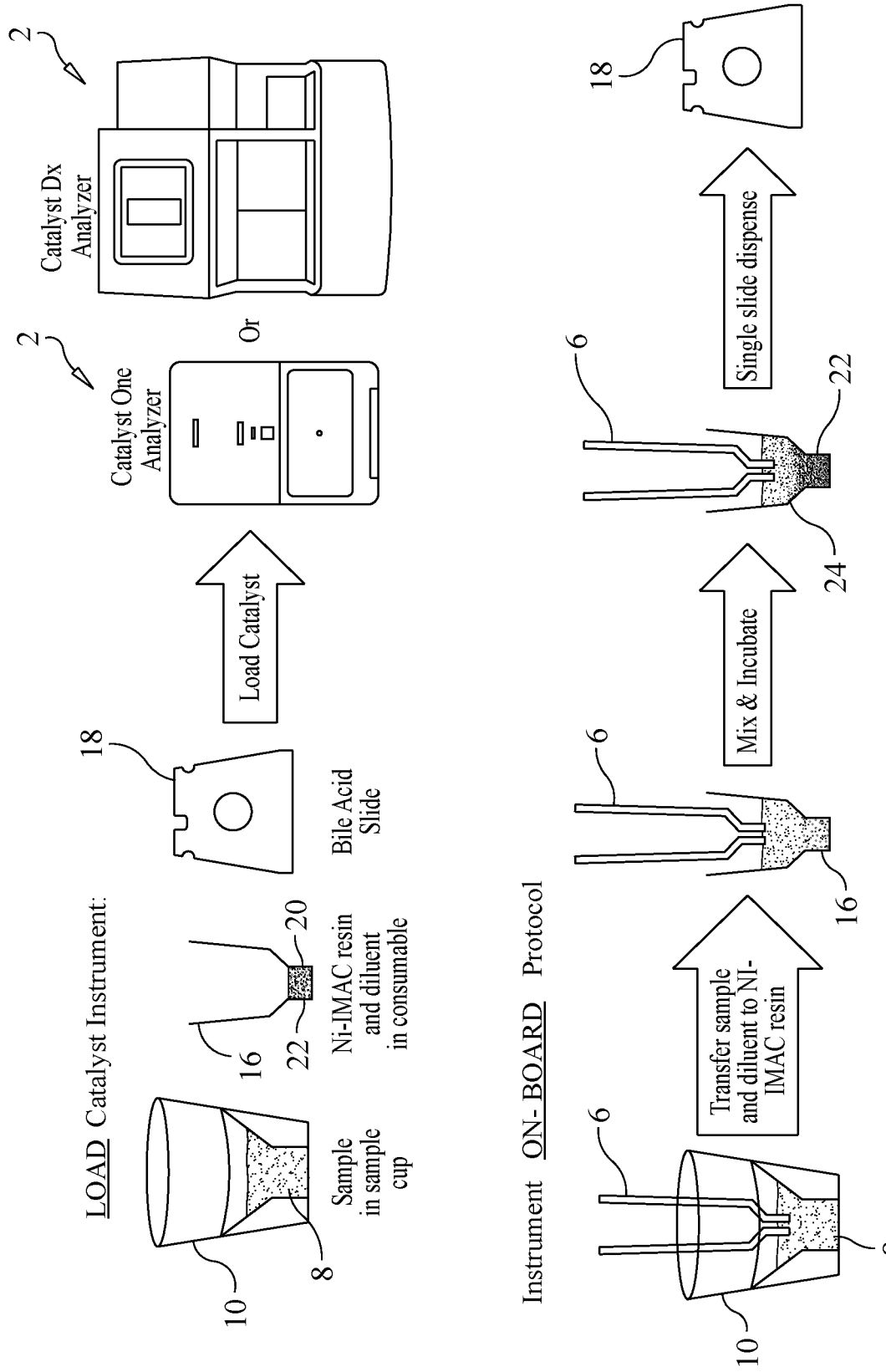
FIG. 3 is pictorial illustration of a sequence of steps taken in accordance with one form of the method of the present invention to remove an interfering component from a liquid sample prior to the sample being dispensed on a test assay.

The preferred sequence of steps in accordance with the present invention, preferably carried out by an automated chemical analyzer 2 having an aspirating/dispensing pipette 4 on which is fitted a disposable tip 6, for treating a liquid sample 8 to remove or at least reduce the content of an interfering component of the liquid sample 8, is illustrated in FIG. 3 of the drawings. Also, reference should be had to U.S. Pat. No. 9,116,129, which issued to Rich, et al. on Aug. 25, 2015 and is titled "Chemical Analyzer"; U.S. Pat. No. 9,797,916, which issued to Connolly, et al. on Oct. 24, 2017 and is titled "Chemical Analyzer"; and U.S. Pat. No. 9,823,109, which issued to Garrepy, et al. on Nov. 21, 2017 and is titled "Chemical Analyzer", which disclose chemical analyzers that are capable of performing the steps of the method of the present invention. The disclosure of each of the aforementioned patents is incorporated herein by reference. Each of the aforementioned patents is assigned of record to IDEXX Laboratories, Inc. of Westbrook, Maine. Chemical analyzers currently available and capable of carrying out the method of the present invention are sold by IDEXX Laboratories, Inc. and are known in the industry by their names, Catalyst One™ and Catalyst Dx™.

In accordance with the sample treatment and interfering component removal method of the present invention, a sample cup 10 containing a liquid sample 8, whole or diluted blood, serum or plasma, for example, is loaded into the chemical analyzer 2. Alternatively, a whole blood sample can be loaded in the centrifuge cup 12 of the whole blood separator 14 of the chemical analyzer 2 and, after centrifugation, plasma or other separated components can be transferred to a consumable mixing cup 16 associated with the chemical analyzer 2 (see the aforementioned U.S. Pat. Nos. 9,116,129; 9,797,916; and 9,823,109 for a description of the blood separator 14, centrifuge cup 12 and mixing cup 16). One or more reagent test slides 18, in this example, bile acid test slides, are also loaded into the chemical analyzer 2. The IMAC resin, containing the porous beads, is stored in a consumable reagent cup which may be used as the mixing cup 16 referred to earlier and above.

More specifically, and in a preferred form, the IMAC resin is lyophilized in a solution of about seven percent (7%) dextran/sucrose, more specifically, about three and one-half percent (3.5%) dextran and about three and one-half percent (3.5%) sucrose, which forms a physically stable cake 20. The dextran/sucrose solution keeps the lyophilized resin cake 20 at the bottom of the mixing cup 16.

The liquid sample 8, for example, blood, serum or plasma, is then transferred by the pipette 4 of the chemical analyzer 2 to the mixing cup 16 by aspirating a volume of the liquid sample 8 from the sample cup 10 into the pipette tip 6 and expelling the volume or a portion thereof from the pipette tip 6 into the mixing cup 16 containing the dried resin cake 20. If it is desired to use a diluted blood sample, then the sample 8 is mixed with preferably a diluent which acts on the resin to put the resin in the optimal state for binding with the interfering component (e.g., hemoglobin, in the case of bile acid assays), the dilution step occurring before or when the blood sample 8 is added to the mixing cup 16 containing the IMAC resin. For example, the pipette tip 6 may first aspirate a first predetermined volume of a diluent buffer, and then aspirate a second predetermined volume of the blood sample 8 from the sample cup 10, and deposit the sample/buffer mixture in the mixing cup 16 in which the resin cake 20 resides. Alternatively, a volume of the liquid sample 8 may first be aspirated and deposited in the mixing cup 16, followed by the diluent buffer being aspirated and deposited in the mixing cup 16 to avoid contact of the diluent buffer in the pipette tip 6 with the liquid sample 8 in the sample cup 10. The liquid sample 8 added to the resin cake 20 residing in the mixing cup 16 will dissolve the cake 20 into a resuspension of the IMAC resin containing the porous beads in the mixing cup 16.

The pipette 4 of the chemical analyzer 2 is then used to mix the liquid sample 8 and IMAC resin beads by aspirating the combined sample/resin solution into the pipette tip 6 and expelling the solution from the pipette tip 6 back into the mixing cup 16, the aspirating step followed by the expelling step being repeated a number of times to ensure that the resuspended resin and sample 8 are thoroughly mixed.

Now, the sample/resin solution in the mixing cup 16 is allowed to rest undisturbed (i.e., incubate) for a predetermined period of time, for example, for about five minutes or less to about ten minutes, or more. This time is determined primarily by the time required for particles to settle out of the liquid fraction for a clean or substantially clean subsequent aspiration by the pipette 4. More dense particles will settle sooner than less dense particles, and so the predetermined period of time for the particles to settle in the mixing cup 16 may vary from about one minute to about fifteen minutes. The interaction between the particles and hemoglobin appears to happen relatively quickly so that an incubation (settling) time of less than or equal to about two minutes to about three minutes may be sufficient. During this incubation time, the hemoglobin, or other targeted interfering component, in the liquid sample, will adhere to the porous beads of the IMAC resin, and the beads, with hemoglobin adhered thereto as well as unattached beads, will settle to the lower bottom portion 22 of the mixing cup 16, as shown in FIGS. 4A and 4B of the drawings, leaving a volume of liquid sample free, or with a minimalized content, of hemoglobin, occupying the upper portion 24 of the mixing cup 16.

Some mixing cups 16 used in automated analyzers and instruments 2 have a distinct geometry, and such geometry should be taken into account when the liquid sample 8, free of the interfering component and occupying the upper portion 24 of the mixing cup 16, is aspirated by the pipette 4 into the tip 6 for dispensing the sample 8 onto the test assay 18. For example, FIGS. 4A and 4B of the drawings illustrate in cross-sectional views the particular preferred frustoconical shape of a mixing cup 16 used with the Catalyst One™ and Catalyst Dx™ IDEXX Laboratories instruments mentioned previously.

Figure 4:
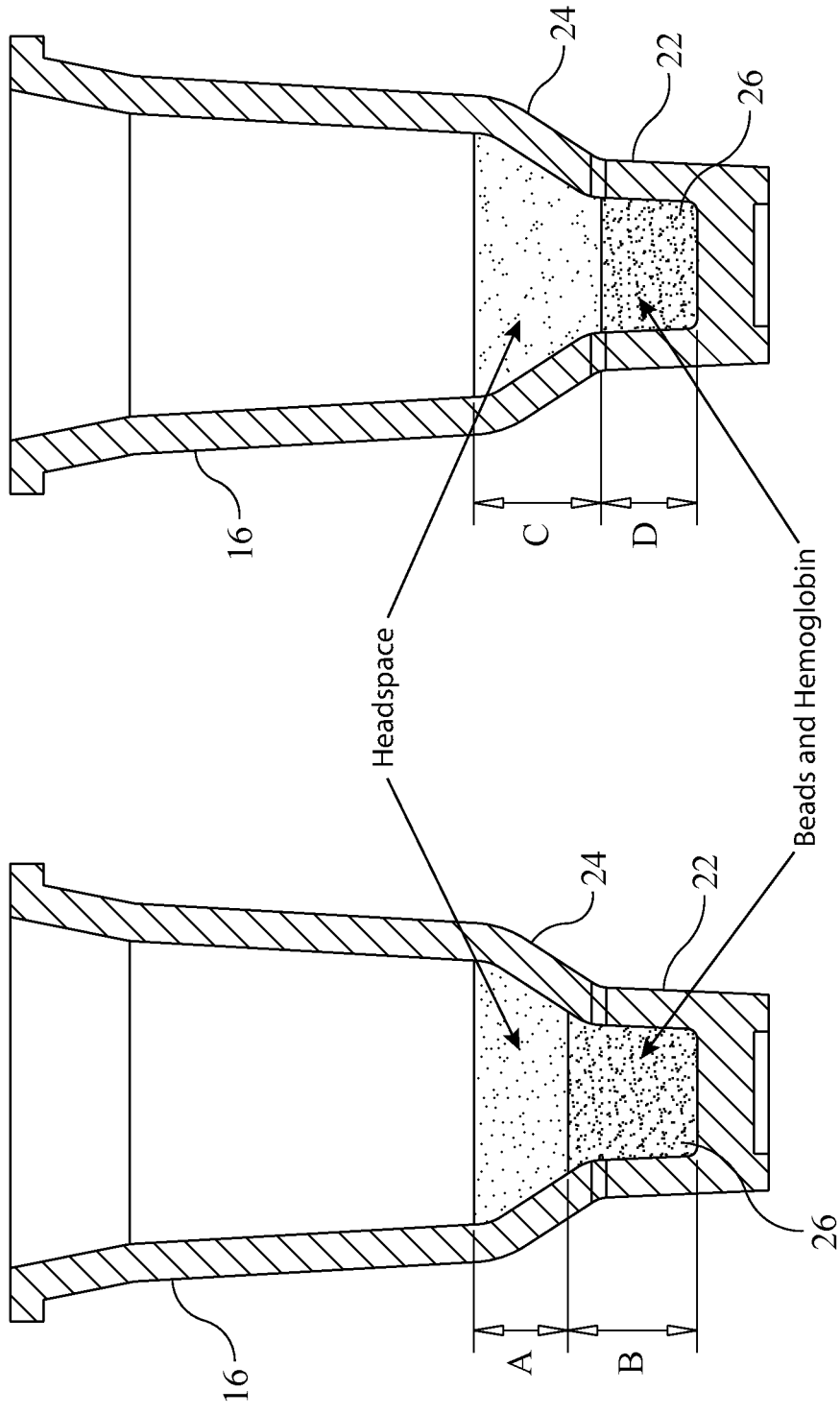
FIG. 4A is a cross-sectional view of a mixing cup used in the method of the present invention containing a mixture of 100 microliters (ul) of liquid sample and 33 microliters (ul) of porous beads dried in the cup and rehydrated by sample.
FIG. 4B is a cross-sectional view of a mixing cup used in the method of the present invention containing a mixture of 100 microliters (ul) of liquid sample and 25 microliters (ul) of porous beads dried in the cup and rehydrated by sample.

In FIG. 4A, the mixing cup 16 is illustrated as containing 100 microliters (ul) of sample and 33 microliters (ul) of resin, dried and rehydrated by sample, and in FIG. 4B, the same mixing cup 16 is illustrated as containing the same volume of sample as illustrated by FIG. 4A but a lesser volume of resin, that is, 100 microliters (ul) of sample and 25 microliters (ul) of resin, dried and rehydrated by sample. In each example of the mixing cup 16 shown in FIGS. 4A and 4B, the volume of particles was lyophilized prior to adding the 100 microliters (ul) of sample, so that the total volume of the sample/bead mix in either example equals about 100 microliters (ul). In other words, once the liquid sample 8 is added to the mixing cup 16, the resin is rehydrated from the sample 8 to nearly its original hydrated volume. Thus, after the predetermined incubation time has elapsed to allow the beads and hemoglobin, or other interfering component, to settle to the lower portion 22 of the mixing cup 16, as illustrated by FIGS. 4A and 4B, the controller of the analyzer 2 should be programmed to cause the pipette tip 6 to be lowered into the mixing cup 16 only to a depth (i.e., vertical height above the cup's internal bottom) necessary to aspirate the liquid sample 8 occupying the upper portion 24 of the mixing cup 16, identified in FIGS. 4A and 4B as the "headspace", so as not to draw into the pipette tip 6 the settled bead/hemoglobin mixture 26 residing in the lower portion 22 of the mixing cup 16.

For example, with the particular geometry of the mixing cup 16 used in IDEXX Laboratories' Catalyst One™ and Catalyst Dx™ instruments and shown in FIGS. 4A and 4B, for a 100 microliter (ul) mixture of sample with 33 μL of rehydrated beads, and after the incubation time has run, the automated instrument 2 should be programmed such that the pipette 4 aspirates some or all of the sample 8 occupying 2.50 millimeters (mm) of vertical "headspace" A residing over 3.40 millimeters (mm) B of a settled solution 26 of beads and hemoglobin (see FIG. 4A), whereas, for a 100 microliter (ul) mixture of sample with 25 μL of rehydrated beads, and after the incubation time has run, the automated instrument 2 should be programmed such that the pipette 4 aspirates some or all of the sample occupying 3.20 millimeters (mm) of vertical "headspace" C residing over 2.70 millimeters (mm) D of a settled solution 26 of beads and hemoglobin (see FIG. 4B). Stated another way, the mixing cup 16 shown in FIG. 4A contains approximately 67 microliters (ul) of available liquid (for testing) and approximately 33 microliters (ul) of rehydrated resin particles for a total volume of approximately 100 microliters (ul), and the mixing cup 16 shown in FIG. 4B contains approximately 75 microliters (ul) of available liquid (for testing) and approximately 25 microliters (ul) of rehydrated resin particles also for a total volume of approximately 100 microliters (ul).

After the solution is allowed to settle in the mixing cup 16 to remove the hemoglobin or other targeted interfering component and any remaining, unattached beads, the pipette 4 of the analyzer 2 aspirates preferably into a new (clean) tip 6 fitted thereon a desired volume of liquid sample 8 only from the upper portion 24 (i.e., the "headspace") of the mixing cup 16 so as to avoid or minimize aspirating settled beads and hemoglobin, each of which may interfere with measurements taken on the test assay 18.

Figure 5:
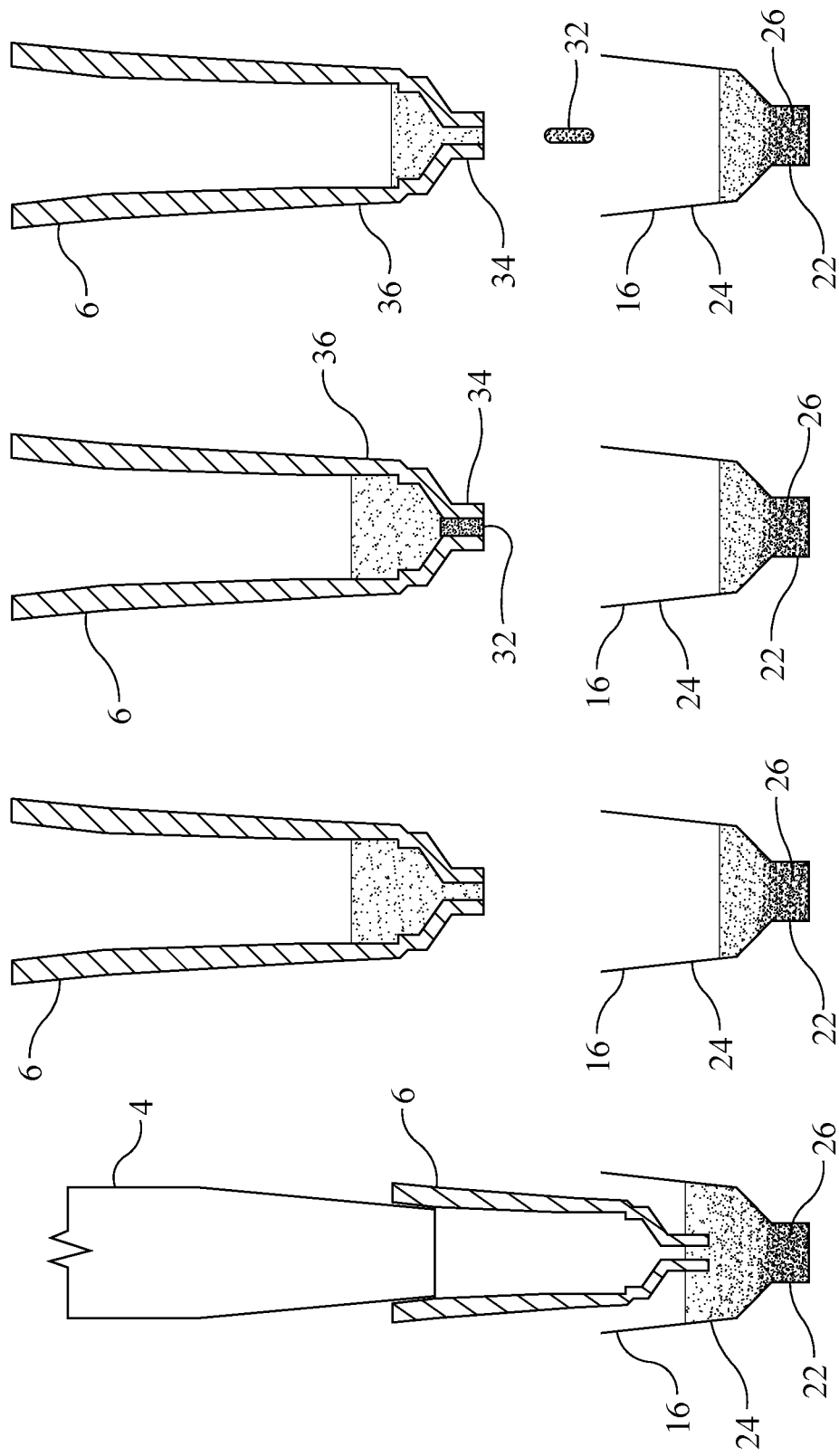
FIG. 5 is a pictorial illustration of a sequence of steps taken in accordance with another form of the method of the present invention to remove an interfering component from a liquid sample prior to the sample being dispensed on a test assay in which any remaining interfering component of a liquid sample residing in the tip of a sample metering pipette may be allowed to settle in the tip and is expelled therefrom and "spit back" into the sample or mixing cup.
Figure 7:
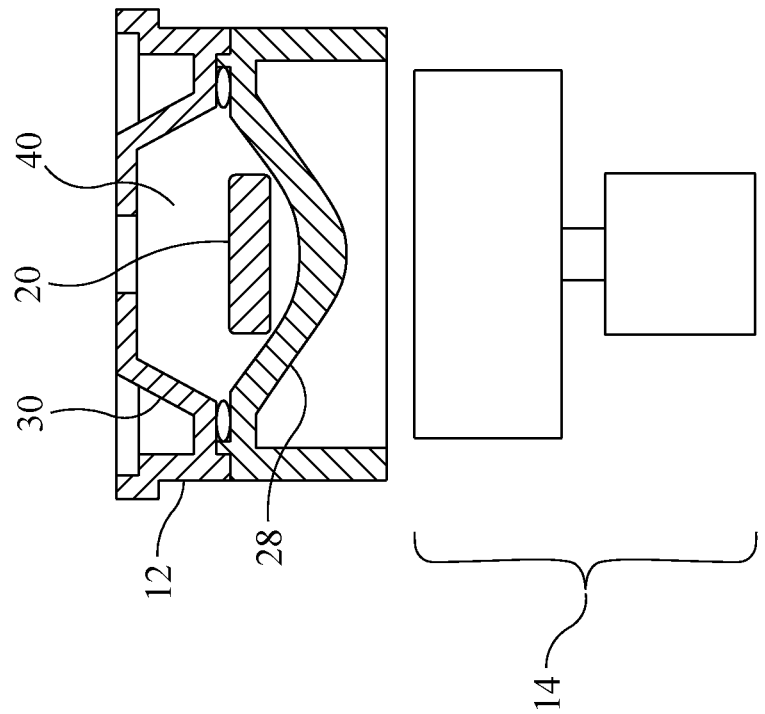
FIG. 7 is a cross-sectional view of one form of a centrifuge cup formed in accordance with the present invention and having an IMAC resin in the form of a physically stable cake situated therein, although it is within the scope of the present invention to have the IMAC resin residing in a liquid form within the centrifuge cup or in a dried form either coating one or more walls of the centrifuge cup, or as constituting part of the gel used for separating components of a whole blood sample during centrifugation, or as the physically stable cake shown herein.

As a precaution, and as an optional step in the method of the present invention, the liquid sample solution 8 aspirated into the pipette tip 6 may be allowed to stand undisturbed for a second predetermined period of incubation time, that is, for about one minute to about fifteen minutes, or for about five minutes or less to about ten minutes or more, or less than or equal to about two minutes to about three minutes (especially for hemoglobin-attached particles to settle), so that, if any beads are present in the aspirated sample solution 8, with or without any remaining interfering component of the liquid sample 8 aspirated into the pipette tip adhered thereto, they will settle to the discharge end of the pipette tip 6. After the time to allow any beads to settle in the pipette tip 6 has elapsed, the controller of the analyzer 2 causes a small volume of the solution in the pipette tip 6, for example, about ten microliters (ul) to about fifty microliters (ul), which includes the settled content which may contain a relatively high concentration of beads, or beads with hemoglobin adhered thereto, to be expelled from the pipette tip 6 and "spit back" into the mixing cup 16 to insure that most all beads and/or leftover hemoglobin are removed from the remaining solution in the pipette tip 6 that is finally dispensed onto the bile acid test slide 18. Such sequence of steps is shown in FIG. 5 of the drawings. Although the bile acid test assay 18 having the sample solution metered thereon is still sensitive to hemoglobin, there remains little or no hemoglobin in the solution that is ultimately dispensed onto the test assay 18 to interfere with the bile acid tests performed and measurements taken by the chemical analyzer 2.

It should be noted that, although it is described herein and shown in the drawings that a consumable mixing cup 16 having a bead/resin cake 20 preloaded therein is preferably used in carrying out the method of the present invention for removing an interfering component from a liquid sample 8, it is envisioned to be within the scope of the present invention to preload the centrifuge cup 12 of the whole blood separator of the chemical analyzer with resin, either in a dried or liquid form, or to add the resin to the centrifuge cup 12 after centrifugation has occurred, whereupon the hemoglobin settles out of the liquid sample 8 towards the bottom 28 of the centrifuge cup 12, and a volume of the sample occupying the upper portion 30 of the centrifuge cup 12 is aspirated by the pipette 4 into the pipette tip 6 for dispensing onto the test assay 18. As before, the sample aspirated by the pipette 4 may be allowed to settle in the pipette tip 6, as shown in FIG. 5, so that any remaining beads may be expelled from the pipette tip 6 before the sample is metered onto the test assay 18. Furthermore, although it is described herein that the resin containing beads resides in the mixing cup 16 as a physically stable cake 20, it is also envisioned that the resin may be in a liquid form that resides in a sealed mixing cup 16, which seal is broken by the downward movement of the pipette tip 6, or resides in a separate, sealed cup and is transferred by the pipette 4 to the mixing cup 16.

The method of removing an interfering component of a liquid sample 8, such as a blood sample (e.g., diluted, undiluted, whole, serum, plasma or the like), will now be further described.

More specifically, and in accordance with one form of the present invention, a method using a chemical analyzer 2 for removing a component of a liquid sample 8 which may interfere with a test performed on a test assay 18 is disclosed herein. The chemical analyzer 2 has associated with it a sample cup 10, a mixing cup 16, and a vertically movable pipette 4 fitted with a disposable pipette tip 6 and capable of aspirating and expelling liquid sample 8 into and from the pipette tip 6 and capable of dispensing the liquid sample 8 onto the test assay 18. The method includes the steps of adding the liquid sample 8 containing the interfering component to the sample cup 10; transferring the liquid sample 8 containing the interfering component from the sample cup 10 to the mixing cup 16, the mixing cup 16 containing an IMAC (Immobilized Metal Affinity Chromatography) resin containing porous beads, the liquid sample 8 and IMAC resin forming a sample/resin solution in the mixing cup 16; mixing the sample/resin solution in the mixing cup 16 using the pipette 4 of the chemical analyzer 2 to achieve a mixed sample/resin solution by aspirating the sample/resin solution into the pipette tip 6 and then expelling the sample/resin solution from the pipette tip 6 into the mixing cup 16, the aspirating and expelling steps being repeated, if or as necessary, to thoroughly mix the sample/resin solution in the mixing cup 16 and achieve the mixed sample/resin solution; allowing the mixed sample/resin solution in the mixing cup 16 to rest undisturbed for a predetermined period of time, the predetermined period of time being selected to allow at least a portion of the interfering component of the liquid sample 8 to adhere to the porous beads of the IMAC resin and to allow at least some of the porous beads with or without the interfering component adhering thereto to settle in the mixing cup and to occupy a bottom portion 22 thereof, the result of the settling of the porous beads having the interfering component adhered thereto being the formation of a refined liquid sample devoid or having a lower concentration of the interfering component than the liquid sample and occupying an upper portion 24 of the mixing cup 16; and aspirating into the pipette tip 6 from the mixing cup 16 a predetermined volume of the refined liquid sample occupying the upper portion 24 of the mixing cup 16 for later dispensing of a selected volume of the refined liquid sample devoid or having the lower concentration of the interfering component onto the test assay 18.

The predetermined period of time mentioned above is preferably between about five minutes and about ten minutes. Furthermore, the IMAC resin preferably includes agarose-based porous beads.

Even more preferably, the IMAC resin is lyophilized in a solution of about two percent (2%) to about fourteen percent (14%) dextran/sucrose or, more preferably, of about seven percent (7%) dextran/sucrose. More particularly, the IMAC resin is lyophilized in a solution of between about two percent (2%) and about ten percent (10%) dextran and between about two percent (2%) and about ten percent (10%) sucrose or, more preferably, of about three and one-half percent (3.5%) dextran and about three and one-half percent (3.5%) sucrose.

In one form, the IMAC resin is formed as a physically stable cake 20 and resides in the bottom portion 22 of the mixing cup 16.

Although the method of the present invention may be used to remove an interfering component from many different types of liquid samples 8 to be analyzed, in one particular application, when a bile acid assay is tested by a chemical analyzer 2, the interfering component that is removed from the liquid sample 8 is hemoglobin.

In yet another form of the present invention, a method is disclosed herein that uses a chemical analyzer 2 for removing a component of a liquid sample 8 which may interfere with a test performed on a test assay 18, where the chemical analyzer 2 has associated therewith a sample cup 10, a mixing cup 16, and a vertically movable pipette 4 fitted with a disposable pipette tip 6 having a discharge end and capable of aspirating and expelling liquid sample 8 into and from the pipette tip 6 and capable of dispensing the liquid sample 8 onto the test assay 18. The method includes the steps of adding the liquid sample 8 containing the interfering component to the sample cup 10; transferring the liquid sample 8 containing the interfering component from the sample cup 10 to the mixing cup 16, the mixing cup 16 containing an IMAC (Immobilized Metal Affinity Chromatography) resin containing porous beads, the liquid sample 8 and IMAC resin forming a sample/resin solution in the mixing cup 16; mixing the sample/resin solution in the mixing cup 16 using the pipette 4 of the chemical analyzer 2 to achieve a mixed sample/resin solution by aspirating the sample/resin solution into the pipette tip 6 and then expelling the sample/resin solution from the pipette tip 6 into the mixing cup 16, the aspirating and expelling steps being repeated, if or as necessary, to thoroughly mix the sample/resin solution in the mixing cup 16 and achieve the mixed sample/resin solution; and allowing the mixed sample/resin solution in the mixing cup 16 to rest undisturbed for a first predetermined period of time, the first predetermined period of time being selected to allow at least a portion of the interfering component of the liquid sample 8 to adhere to the porous beads of the IMAC resin and to allow at least some of the porous beads with or without the interfering component adhering thereto to settle in the mixing cup 16 and to occupy a bottom portion 22 thereof, the result of the settling of the porous beads having the interfering component adhered thereto being the formation of a first stage refined liquid sample devoid or having a first lower concentration of the interfering component than the liquid sample 8 and occupying an upper portion 24 of the mixing cup 16.

The method further includes the steps of aspirating into the pipette tip 6 from the mixing cup 16 a predetermined volume of the first stage refined liquid sample occupying the upper portion 24 of the mixing cup 16; allowing the first stage refined liquid sample aspirated into the pipette tip 6 to rest undisturbed for a second predetermined period of time, the second predetermined period of time being selected to allow any remaining interfering component of the liquid sample in the first stage refined liquid sample in the pipette tip 6 to adhere to any porous beads of the IMAC resin remaining in the first stage refined liquid sample in the pipette tip 6 and to allow at least some of the remaining porous beads with or without the interfering component adhering thereto to settle in the pipette tip 6 and to form a settled solution 32 occupying a bottom portion 34 of the pipette tip 6 near the discharge end thereof, the result of the settling of the porous beads having the interfering component adhered thereto and unattached porous beads being the formation of the settled solution 32 and a second stage, more refined liquid sample devoid or having a second lower concentration of the interfering component than the first stage refined liquid sample and occupying an upper portion 36 of the pipette tip 6; and expelling from the pipette tip 6 the settled solution 32 occupying the bottom portion 34 of the pipette tip 6 into the mixing cup 16, leaving the second stage, more refined liquid sample in the pipette tip 6 for later dispensing of a selected volume of the second stage, more refined liquid sample devoid or having the second lower concentration of the interfering component onto the test assay 18.

In the method described above, the first predetermined period of time is preferably between about five minutes and about ten minutes, and the second predetermined period of time is preferably between about five minutes and about ten minutes; the IMAC resin may include agarose-based porous beads; the IMAC resin is preferably lyophilized in a solution of about seven percent (7%) dextran/sucrose; even more preferably, the IMAC resin is lyophilized in a solution of about three and one-half percent (3.5%) dextran and about three and one-half percent (3.5%) sucrose, wherein the IMAC resin is formed as a physically stable cake 20 and resides in the bottom portion 22 of the mixing cup 16; and wherein the method is used to remove hemoglobin as the interfering component that may affect tests performed on a bile acid test assay 18.

In accordance with yet another form of the method of the present invention for removing a component of a blood sample 8 which may interfere with a test performed on a test assay 18, again, a chemical analyzer 2 is used. The chemical analyzer 2 has a blood separator 14 and a centrifuge cup 12, a mixing cup 16 and a vertically movable pipette 4 fitted with a disposable pipette tip 6 and capable of aspirating and expelling a liquid into and from the pipette tip 6 and capable of dispensing a liquid onto the test assay 18. The method includes the steps of adding the blood sample 8 containing the interfering component to the centrifuge cup 12; centrifuging the blood sample in the centrifuge cup 12 using the blood separator 14 of the chemical analyzer 2 to provide a separated blood component in the centrifuge cup 12, the separated blood component containing the interfering component; transferring the separated blood component containing the interfering component from the centrifuge cup 12 to the mixing cup 16, the mixing cup 16 containing an IMAC (Immobilized Metal Affinity Chromatography) resin containing porous beads, the separated blood component and IMAC resin forming a blood component/resin solution in the mixing cup 16; mixing the blood component/resin solution in the mixing cup 16 using the pipette 4 of the chemical analyzer 2 to achieve a mixed blood component/resin solution by aspirating the blood component/resin solution into the pipette tip 6 and then expelling the blood component/resin solution from the pipette tip 6 into the mixing cup 16, the aspirating and expelling steps being repeated, if or as necessary, to thoroughly mix the blood component/resin solution in the mixing cup 16 and achieve the mixed blood component/resin solution; allowing the mixed blood component/resin solution in the mixing cup 16 to rest undisturbed for a predetermined period of time, the predetermined period of time being selected to allow at least a portion of the interfering component of the blood component to adhere to the porous beads of the IMAC resin and to allow at least some of the porous beads with or without the interfering component adhering thereto to settle in the mixing cup 16 and to occupy a bottom portion 22 thereof, the result of the settling of the porous beads having the interfering component adhered thereto being the formation of a refined blood component devoid or having a lower concentration of the interfering component than the blood component and occupying an upper portion 24 of the mixing cup 16; and aspirating into the pipette tip 6 from the mixing cup 16 a predetermined volume of the refined blood component occupying the upper portion of the mixing cup 16 for later dispensing of a selected volume of the refined blood component devoid or having the lower concentration of the interfering component onto the test assay 18.

In accordance with the method described above, the predetermined period of time is preferably between about five minutes and about ten minutes; the IMAC resin may include agarose-based porous beads; the IMAC resin is preferably lyophilized in a solution of about seven percent (7%) dextran/sucrose; even more preferably, the IMAC resin is lyophilized in a solution of about three and one-half percent (3.5%) dextran and about three and one-half percent (3.5%) sucrose, wherein the IMAC resin is formed as a physically stable cake 20 and resides in the bottom portion 22 of the mixing cup 16; and wherein the method is used to remove hemoglobin as the interfering component that may affect tests performed on a bile acid test assay 18.

In accordance with yet another form of the method of the present invention for removing a component of a blood sample 8 which may interfere with a test performed on a test assay 18, a chemical analyzer 2 is used that has a blood separator 14 and a centrifuge cup 12, a mixing cup 16, and a vertically movable pipette 4 fitted with a disposable pipette tip 6 having a discharge end and capable of aspirating and expelling a liquid into and from the pipette tip 6 and capable of dispensing a liquid onto the test assay 18. The method includes the steps of adding the blood sample 8 containing the interfering component to the centrifuge cup 12; centrifuging the blood sample 8 in the centrifuge cup 12 using the blood separator 14 of the chemical analyzer 2 to provide a separated blood component in the centrifuge cup 12, the separated blood component containing the interfering component; transferring the separated blood component containing the interfering component from the centrifuge cup 12 to the mixing cup 16, the mixing cup 16 containing an IMAC (Immobilized Metal Affinity Chromatography) resin containing porous beads, the separated blood component and IMAC resin forming a blood component/resin solution in the mixing cup 16; mixing the blood component/resin solution in the mixing cup 16 using the pipette 4 of the chemical analyzer 2 to achieve a mixed blood component/resin solution by aspirating the blood component/resin solution into the pipette tip 6 and then expelling the blood component/resin solution from the pipette tip 6 into the mixing cup 16, the aspirating and expelling steps being repeated, if or as necessary, to thoroughly mix the blood component/resin solution in the mixing cup 16 and achieve the mixed blood component/resin solution; and allowing the mixed blood component/resin solution in the mixing cup 16 to rest undisturbed for a first predetermined period of time, the first predetermined period of time being selected to allow at least a portion of the interfering component of the blood component to adhere to the porous beads of the IMAC resin and to allow at least some of the porous beads with or without the interfering component adhering thereto to settle in the mixing cup 16 and to occupy a bottom portion 22 thereof, the result of the settling of the porous beads having the interfering component adhered thereto being the formation of a first stage refined blood component devoid or having a first lower concentration of the interfering component than the blood component and occupying an upper portion 24 of the mixing cup 16.

The method further includes the steps of aspirating into the pipette tip 6 from the mixing cup 16 a predetermined volume of the first stage refined blood component occupying the upper portion 24 of the mixing cup 16; allowing the first stage refined blood component aspirated into the pipette tip 6 to rest undisturbed for a second predetermined period of time, the second predetermined period of time being selected to allow any remaining interfering component of the blood component in the first stage refined blood component in the pipette tip 6 to adhere to any porous beads of the IMAC resin remaining in the first stage refined blood component in the pipette tip 6 and to allow at least some of the remaining porous beads with or without the interfering component adhering thereto to settle in the pipette tip 6 and to form a settled solution 32 occupying a bottom portion 34 of the pipette tip 6 near the discharge end thereof, the result of the settling of the porous beads having the interfering component adhered thereto and unattached porous beads is the formation of the settled solution 32 and a second stage, more refined blood component devoid or having a second lower concentration of the interfering component than the first refined blood component and occupying an upper portion 36 of the pipette tip 6; and expelling from the pipette tip 6 the settled solution 32 occupying the bottom portion 34 of the pipette tip 6 into the mixing cup 16, leaving the second stage, more refined blood component in the pipette tip 6 for later dispensing of a selected volume of the second stage, more refined blood component devoid or having the second lower concentration of the interfering component onto the test assay 18.

In accordance with the method described above, the first predetermined period of time is preferably between about five minutes and about ten minutes, and the second predetermined period of time is preferably between about five minutes and about ten minutes; the IMAC resin may include agarose-based porous beads; the IMAC resin is preferably lyophilized in a solution of about seven percent (7%) dextran/sucrose; even more preferably, the IMAC resin is lyophilized in a solution of about three and one-half percent (3.5%) dextran and about three and one-half percent (3.5%) sucrose, wherein the IMAC resin is formed as a physically stable cake 20 and resides in the bottom portion 22 of the mixing cup 16; and wherein the method is used to remove hemoglobin as the interfering component that may affect tests performed on a bile acid test assay 18.

The present invention is also directed to an IMAC (Immobilized Metal Affinity Chromatography) resin containing porous beads and used in a chemical analyzer 2 for removing a component of a liquid sample 8 which may interfere with a test performed on a test assay 18 by the chemical analyzer 2. The IMAC resin is lyophilized in a solution of about three and one-half percent (3.5%) dextran and about three and one-half percent (3.5%) sucrose to form a physically stable cake 20.

Figure 6:
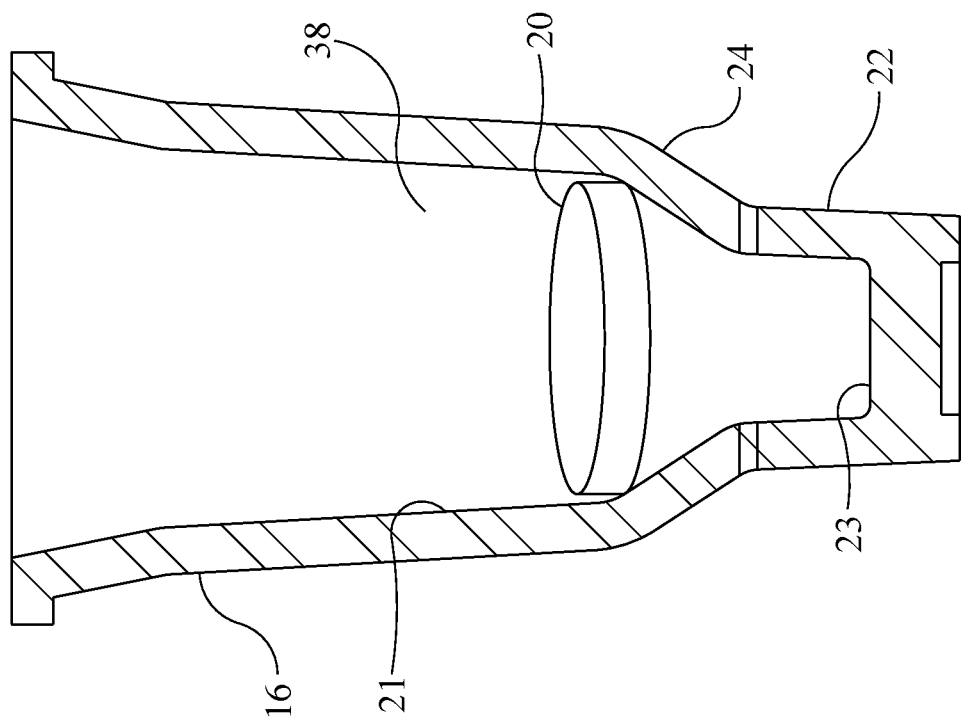
FIG. 6 is a cross-sectional view of one form of a mixing cup formed in accordance with the present invention and having an IMAC resin in the form of a physically stable cake situated therein, although it is within the scope of the present invention to have the IMAC resin residing in a liquid form within the mixing cup or in a dried form either coating one or more walls of the mixing cup or as the physically stable cake shown herein.

The present invention is further directed to a mixing cup 16, such as shown in FIG. 6, used for mixing a liquid sample 8 in a chemical analyzer 2, the mixing cup 16 having an interior space 38. The mixing cup 16 includes an IMAC (Immobilized Metal Affinity Chromatography) resin containing porous beads and used by the chemical analyzer 2 for removing a component of the liquid sample 8 which may interfere with a test performed on a test assay 18 by the chemical analyzer 2, the IMAC resin being situated within the interior space 38 of the mixing cup 16.

Even more preferably, the mixing cup 16 used for mixing a liquid sample 8 in a chemical analyzer 2 includes a bottom portion 22 and an upper portion 24 situated above the bottom portion 22, and an IMAC (Immobilized Metal Affinity Chromatography) resin containing porous beads and used by the chemical analyzer 2 for removing a component of the liquid sample 8 which may interfere with a test performed on a test assay 18 by the chemical analyzer 2. The IMAC resin is lyophilized in a solution of about three and one-half percent (3.5%) dextran and about three and one-half percent (3.5%) sucrose to form a physically stable cake 20, the resin cake 20 residing in the bottom portion 22 of the mixing cup 16. The resin cake 20 is resuspended in a liquid form when the liquid sample 8 is added to the mixing cup 16 to form a sample/resin solution therein, wherein, when the sample/resin solution in the mixing cup 16 is mixed, a mixed sample/resin solution is achieved, and wherein, when the mixed sample/resin solution in the mixing cup 16 is allowed to rest undisturbed for a predetermined period of time, at least a portion of the interfering component of the liquid sample 8 adheres to the porous beads of the IMAC resin and at least some of the porous beads with or without the interfering component adhering thereto settle in the mixing cup 16 and occupy the bottom portion 22 thereof. The result of the settling of the porous beads having the interfering component adhered thereto is the formation of a refined liquid sample devoid or having a lower concentration of the interfering component than the liquid sample 8 and occupying the upper portion 24 of the mixing cup 16. The refined liquid sample occupying the upper portion 24 of the mixing cup 16 is provided for later dispensing of a selected volume of the refined liquid sample devoid or having the lower concentration of the interfering component onto the test assay 18.

Even more specifically, a mixing cup 16 used for mixing a liquid sample 8 in a chemical analyzer 2 includes an interior space 38 and further includes a resin containing beads and used by the chemical analyzer 2 for removing a component of the liquid sample 8 which may interfere with a test performed on a test assay 18 by the chemical analyzer 2. The resin is situated within the interior space 38 of the mixing cup 16. Preferably, the resin is an IMAC (Immobilized Metal Affinity Chromatography) resin.

In one form, the mixing cup 16 includes an interior side wall 21 and a bottom wall 23, and the resin is lyophilized. The lyophilized resin coats at least one of at least a portion of the interior side wall 21 of the mixing cup 16 and at least a portion of the bottom wall 23 of the mixing cup 16.

In yet another form, the mixing cup 16 further includes a bottom portion 22 and an upper portion 24 situated above the bottom portion 22. The lyophilized resin is resuspended in a liquid form when the liquid sample 8 is added to the mixing cup 16 to form a sample/resin solution therein, wherein, when the sample/resin solution in the mixing cup 16 is mixed, a mixed sample/resin solution is achieved, and wherein, when the mixed sample/resin solution in the mixing cup 16 is allowed to rest undisturbed for a predetermined period of time, at least a portion of the interfering component of the liquid sample 8 adheres to the beads of the resin and at least some of the beads with or without the interfering component adhering thereto settle in the mixing cup 16 and occupy the bottom portion 22 thereof, the result of the settling of the beads having the interfering component adhered thereto being the formation of a refined liquid sample devoid or having a lower concentration of the interfering component than the liquid sample 8 and occupying an upper portion 24 of the mixing cup 16, the refined liquid sample occupying the upper portion 24 of the mixing cup 16 being provided for later dispensing of a selected volume of the refined liquid sample devoid or having the lower concentration of the interfering component onto the test assay 18.

Preferably, the predetermined period of time which the mixed sample/resin solution in the mixing cup 16 is allowed to rest undisturbed is between about one minute and about fifteen minutes. Furthermore, the resin preferably includes at least one of agarose-based beads and silica-based beads. Also, preferably the test assay 18 is a bile acid assay, and the interfering component of the liquid sample is hemoglobin.

Additionally, the resin is lyophilized in a solution of between about two percent (2%) and about ten percent (10%) dextran and between about two percent (2%) and about ten percent (10%) sucrose, or the resin is lyophilized in a solution of about two percent (2%) to about fourteen percent (14%) dextran/sucrose.

In yet another form of the present invention, the resin in the mixing cup 16 is lyophilized and forms a physically stable cake 20, the resin cake 20 being situated within the interior space 38 of the mixing cup 16. Furthermore, the mixing cup 16 further includes a bottom portion 22 and an upper portion 24 situated above the bottom portion 22. The resin cake 20 is resuspended in a liquid form when the liquid sample 8 is added to the mixing cup 16 to form a sample/resin solution therein, wherein, when the sample/resin solution in the mixing cup 16 is mixed, a mixed sample/resin solution is achieved, and wherein, when the mixed sample/resin solution in the mixing cup 16 is allowed to rest undisturbed for a predetermined period of time, at least a portion of the interfering component of the liquid sample 8 adheres to the beads of the resin and at least some of the beads with or without the interfering component adhering thereto settle in the mixing cup 16 and occupy the bottom portion 22 thereof, the result of the settling of the beads having the interfering component adhered thereto being the formation of a refined liquid sample devoid or having a lower concentration of the interfering component than the liquid sample 8 and occupying an upper portion 24 of the mixing cup 16, the refined liquid sample occupying the upper portion 24 of the mixing cup 16 being provided for later dispensing of a selected volume of the refined liquid sample devoid or having the lower concentration of the interfering component onto the test assay 18.

Preferably, the resin is lyophilized in a solution of between about two percent (2%) and about ten percent (10%) dextran and between about two percent (2%) and about ten percent (10%) sucrose, or the resin is lyophilized in a solution of about two percent (2%) to about fourteen percent (14%) dextran/sucrose.

Furthermore, the predetermined period of time which the mixed sample/resin solution in the mixing cup 16 is allowed to rest undisturbed is between about one minute and about fifteen minutes, and the resin includes at least one of agarose-based beads and silica-based beads.

Also, the test assay 18 may be a bile acid assay, and the interfering component of the liquid sample 8 may be hemoglobin.

In yet another form of the present invention, a mixing cup 16 used for mixing a liquid sample 8 in a chemical analyzer 2 includes an interior space 38, a bottom portion 22 and an upper portion 24 situated above the bottom portion 22, and a resin containing beads and used by the chemical analyzer 2 for removing a component of the liquid sample 8 which may interfere with a test performed on a test assay 18 by the chemical analyzer 2. The resin is situated within the interior space 38 of the mixing cup 16. Preferably, the resin is an IMAC (Immobilized Metal Affinity Chromatography) resin.

Preferably, the resin is lyophilized in a solution of between about two percent (2%) and about ten percent (10%) dextran and between about two percent (2%) and about ten percent (10%) sucrose, or of about two percent (2%) to about fourteen percent (14%) dextran/sucrose, to form a physically stable cake 20, the resin cake 20 residing in the bottom portion 22 of the mixing cup 16, the resin cake 20 being resuspended in a liquid form when the liquid sample 8 is added to the mixing cup 16 to form a sample/resin solution therein, wherein, when the sample/resin solution in the mixing cup 16 is mixed, a mixed sample/resin solution is achieved, and wherein, when the mixed sample/resin solution in the mixing cup 16 is allowed to rest undisturbed for a predetermined period of time, at least a portion of the interfering component of the liquid sample 8 adheres to the beads of the resin and at least some of the beads with or without the interfering component adhering thereto settle in the mixing cup 16 and occupy the bottom portion 22 thereof, the result of the settling of the beads having the interfering component adhered thereto being the formation of a refined liquid sample devoid or having a lower concentration of the interfering component than the liquid sample 8 and occupying an upper portion 24 of the mixing cup 16, the refined liquid sample occupying the upper portion 24 of the mixing cup 16 being provided for later dispensing of a selected volume of the refined liquid sample devoid or having the lower concentration of the interfering component onto the test assay 18.

The present invention is also directed to a centrifuge cup 12 of a blood separator 14 forming part of a chemical analyzer 2 and used for centrifuging a blood sample 8 contained therein to provide a separated blood component in the centrifuge cup 12, the centrifuge cup 12 having an interior space 40. Preferably, the centrifuge cup 12 includes an IMAC (Immobilized Metal Affinity Chromatography) resin containing porous beads and used by the chemical analyzer 2 for removing a component of the blood sample 8 which may interfere with a test performed on a test assay 18 by the chemical analyzer 2, the IMAC resin being situated within the interior space 40 of the centrifuge cup 12. The IMAC resin may reside in the interior space 40 of the centrifuge cup 12 in either liquid form, a dried form adhering to a wall or walls of the centrifuge cup 12 or as a physically stable cake 20, as will be described below.

More specifically, the centrifuge cup 12 of the blood separator 14 includes an IMAC (Immobilized Metal Affinity Chromatography) resin containing porous beads and used by the chemical analyzer 2 for removing a component of the separated blood component which may interfere with a test performed on a test assay 18 by the chemical analyzer 2, the IMAC resin being lyophilized in a solution of about three and one-half percent (3.5%) dextran and about three and one-half percent (3.5%) sucrose to form a physically stable cake 20, the resin cake 20 residing in the interior space 40 of the centrifuge cup 12. The resin cake 20 is resuspended in a liquid form when the separated blood component is present in the centrifuge cup 12 to form a blood component/resin solution therein, wherein, when the blood component/resin solution in the centrifuge cup 12 is mixed, a mixed blood component/resin solution is achieved, and wherein, when the mixed blood component/resin solution in the centrifuge cup 12 is allowed to rest undisturbed for a predetermined period of time, at least a portion of the interfering component of the blood component adheres to the porous beads of the IMAC resin and at least some of the porous beads with or without the interfering component adhering thereto will settle in the centrifuge cup 12 and occupy a bottom portion 28 of the interior space 40 of the centrifuge cup 12. The result of the settling of the porous beads having the interfering component adhered thereto is the formation of a refined blood component devoid or having a lower concentration of the interfering component than the blood sample 8 and occupying an upper portion 30 of the centrifuge cup 12. The refined blood component occupying the upper portion 30 of the centrifuge cup 12 is provided for later dispensing of a selected volume of the refined blood component devoid or having the lower concentration of the interfering component onto the test assay 18.

Figure 8A:
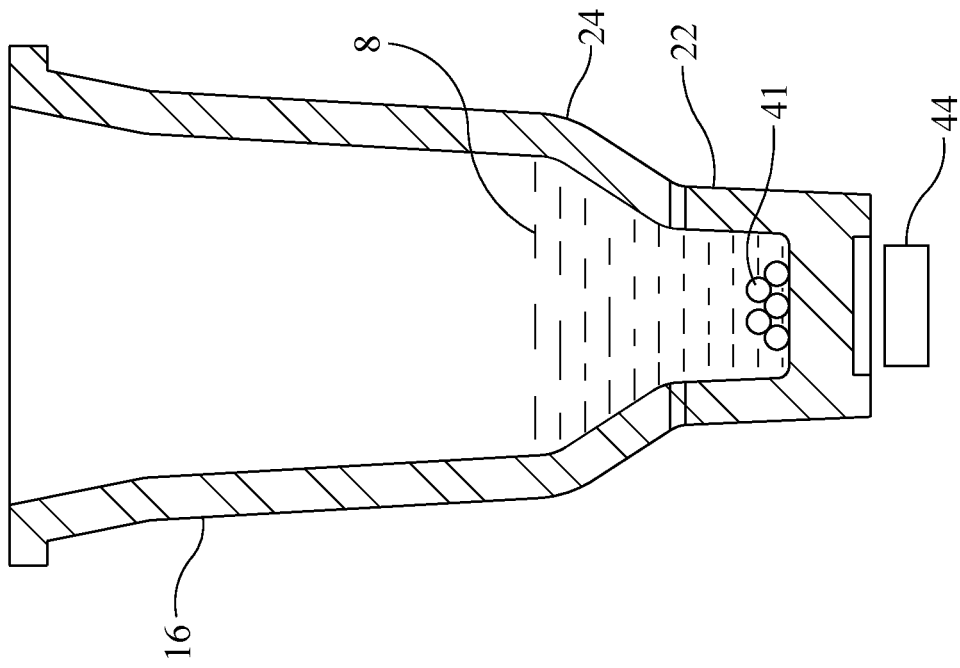
FIG. 8A is a cross-sectional view of another form of a mixing cup formed in accordance with the present invention and having functionalized magnetic or ferrous particles and a magnet residing within the cup, and illustrating how components of a liquid sample, such as hemoglobin in a blood sample, in the mixing cup adhere to the functionalized magnetic or ferrous particles which are thereby pulled with the particles to the magnet by magnetic attraction.
Figure 8B:
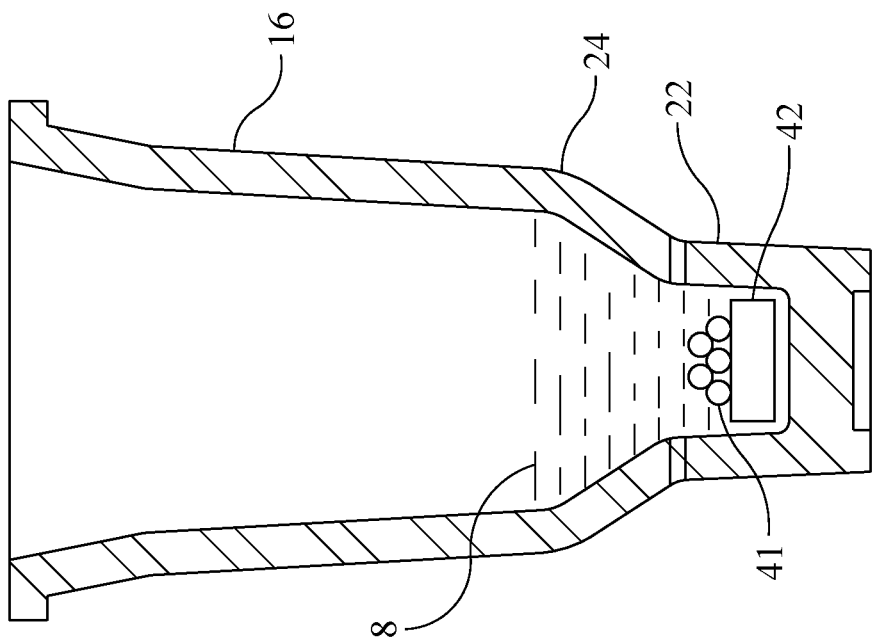
FIG. 8B is a cross-sectional view of another form of a mixing cup formed in accordance with the present invention and having functionalized magnetic or ferrous particles and a magnet residing outside the cup, and illustrating how components of a liquid sample, such as hemoglobin in a blood sample, in the mixing cup adhere to the functionalized magnetic or ferrous particles which are thereby pulled with the particles to the magnet by magnetic attraction.

FIGS. 8A and 8B illustrate another method of removing an interfering component of a liquid sample in accordance with the present invention. The functionalized beads or particles 41 may be formed to have magnetic properties, or have ferrous components, or more generally, be magnetically attractable to a permanent magnet 42 residing within the lower portion 22 of the mixing cup 16, as shown in FIG. 8A, or a permanent magnet or electromagnet 44 positioned outside and preferably under the bottom of the cup 16, as shown in FIG. 8B. The cup 16, being formed of a non-magnetic, preferably thermoplastic material, will not interfere with the magnetic attraction between the functionalized magnetic particles or beads 41 and the magnet or electromagnet 42, 44 placed inside the cup 16 or outside and in close proximity to the cup 16. The functionalized particles 41 may be in dried form and coated on the walls of the mixing cup 16, or may come in a physically stable form 20 and reside in the cup 16, as previously described herein and shown in FIG. 6 of the drawings.

When a liquid sample 8 is added to the mixing cup 16, the functionalized magnetic particles 41 are rehydrated and mix in solution with the liquid sample 8. The interfering component of the liquid sample 8 to be removed therefrom adheres to the functionalized magnetic particles 41 which, in turn, are magnetically attracted and drawn to the magnet 42, 44 residing in the lower portion 22 of the cup 16 or underneath and in close proximity to the bottom of the cup 16. Thus, the particles or beads 41, with the interfering component adhered thereto, or particles or beads 41 having no sample component adhering thereto, will by attraction to the magnet 42, 44 occupy the lower portion 22 of the cup 16, leaving a volume of the liquid sample 8, free of the interfering component or having a reduced concentration thereof, occupying the upper portion 24 of the mixing cup 16, where it may be easily aspirated into the pipette tip 6 to be subsequently deposited on a chemical reagent test slide 18.

Suitable functionalized particles having such magnetic properties are beads having Part No. 88831 distributed by Thermo Fisher Scientific Inc. of Waltham, MA.

Although it is primarily described herein that the gel containing functionalized particles is placed in a mixing cup 16 used by an automated chemical analyzer 2, it is envisioned to place the gel in a sample cup, reagent cup, centrifuge cup or any other type of cup or liquid holding vessel that may be used to remove an interfering component of the liquid sample 8 or reduce the concentration thereof in the liquid sample 8, and it should be understood that the term "mixing cup" used herein and in the claims should be interpreted to include all of the aforementioned cups and vessels.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A mixing cup used for mixing a liquid sample in a chemical analyzer, wherein the mixing cup comprises:
   an interior space;
   an interior side wall and a bottom wall; and
   a resin containing beads and used by the chemical analyzer for removing an interfering component of the liquid sample which may interfere with a test performed on a test assay by the chemical analyzer, wherein the resin is situated within the interior space of the mixing cup,
   wherein the resin is lyophilized in a solution of between about two percent (2%) and about ten percent (10%) dextran and between about two percent (2%) and about ten percent (10%) sucrose, or of about two percent (2%) to about fourteen percent (14%) dextran/sucrose; and
   wherein the lyophilized resin coats at least one of at least a portion of the interior side wall of the mixing cup and at least a portion of the bottom wall of the mixing cup.

2. The mixing cup of claim 1, wherein the resin is an IMAC (Immobilized Metal Affinity Chromatography) resin.

3. The mixing cup of claim 1, which further comprises:
   a bottom portion and an upper portion situated above the bottom portion;
   wherein the lyophilized resin is resuspended in a liquid form when the liquid sample is added to the mixing cup to form a sample/resin solution therein, and wherein, when the sample/resin solution in the mixing cup is mixed, a mixed sample/resin solution is achieved, and wherein, when the mixed sample/resin solution in the mixing cup is allowed to rest undisturbed for a predetermined period of time, at least a portion of the interfering component of the liquid sample adheres to the beads of the resin and at least some of the beads settle in the mixing cup and occupy the bottom portion thereof, the result of the settling of the beads having the interfering component adhered thereto being the formation of a refined liquid sample devoid or having a lower concentration of the interfering component than the liquid sample and occupying an upper portion of the mixing cup, the refined liquid sample occupying the upper portion of the mixing cup being provided for later dispensing of a selected volume of the refined liquid sample devoid or having the lower concentration of the interfering component onto the test assay.

4. The mixing cup of claim 3, wherein the predetermined period of time which the mixed sample/resin solution in the mixing cup is allowed to rest undisturbed is between about one minute and about fifteen minutes.

5. The mixing cup of claim 1, wherein the resin includes at least one of agarose-based beads and silica-based beads.

6. The mixing cup of claim 1, wherein the test assay is a bile acid assay; and
   wherein the interfering component of the liquid sample is hemoglobin.

7. A mixing cup used for mixing a liquid sample in a chemical analyzer, the mixing cup having an interior space, the mixing cup comprising:
   a resin containing beads and used by the chemical analyzer for removing an interfering component of the liquid sample which may interfere with a test performed on a test assay by the chemical analyzer, wherein the resin is situated within the interior space of the mixing cup; and
   wherein the resin is lyophilized in a solution of between about two percent (2%) and about ten percent (10%) dextran and between about two percent (2%) and about ten percent (10%) sucrose, or of about two percent (2%) to about fourteen percent (14%) dextran/sucrose and forms a physically stable cake within the interior space of the mixing cup.

8. The mixing cup of claim 7, which further comprises:
   a bottom portion and an upper portion situated above the bottom portion;
   wherein the physically stable cake is resuspended in a liquid form when the liquid sample is added to the mixing cup to form a sample/resin solution therein, and wherein, when the sample/resin solution in the mixing cup is mixed, a mixed sample/resin solution is achieved, and wherein, when the mixed sample/resin solution in the mixing cup is allowed to rest undisturbed for a predetermined period of time, at least a portion of the interfering component of the liquid sample adheres to the beads of the resin and at least some of the beads settle in the mixing cup and occupy the bottom portion thereof, the result of the settling of the beads having the interfering component adhered thereto being the formation of a refined liquid sample devoid or having a lower concentration of the interfering component than the liquid sample and occupying an upper portion of the mixing cup, the refined liquid sample occupying the upper portion of the mixing cup being provided for later dispensing of a selected volume of the refined liquid sample devoid or having the lower concentration of the interfering component onto the test assay.

9. The mixing cup of claim 8, wherein the predetermined period of time which the mixed sample/resin solution in the mixing cup is allowed to rest undisturbed is between about one minute and about fifteen minutes.

10. The mixing cup of claim 7, wherein the resin includes at least one of agarose-based beads and silica-based beads.

11. The mixing cup of claim 7, wherein the test assay is a bile acid assay; and wherein the interfering component of the liquid sample is hemoglobin.

12. A mixing cup used for mixing a liquid sample in a chemical analyzer, the mixing cup having an interior space, the mixing cup comprising:
   a resin containing beads and used by the chemical analyzer for removing an interfering component of the liquid sample which may interfere with a test performed on a test assay by the chemical analyzer, wherein the resin is situated within the interior space of the mixing cup;
   a bottom portion and an upper portion situated above the bottom portion; and
   wherein the resin is lyophilized in a solution of between about two percent (2%) and about ten percent (10%) dextran and between about two percent (2%) and about ten percent (10%) sucrose, or of about two percent (2%) to about fourteen percent (14%) dextran/sucrose, to form a physically stable cake, and wherein the physically stable cake resides in the interior space of the mixing cup and is resuspended in a liquid form when the liquid sample is added to the mixing cup to form a sample/resin solution therein, and wherein, when the sample/resin solution in the mixing cup is mixed, a mixed sample/resin solution is achieved, and wherein, when the mixed sample/resin solution in the mixing cup is allowed to rest undisturbed for a predetermined period of time, at least a portion of the interfering component of the liquid sample adheres to the beads of the resin and at least some of the beads settle in the mixing cup and occupy the bottom portion thereof, the result of the settling of the beads having the interfering component adhered thereto being the formation of a refined liquid sample devoid or having a lower concentration of the interfering component than the liquid sample and occupying an upper portion of the mixing cup, the refined liquid sample occupying the upper portion of the mixing cup being provided for later dispensing of a selected volume of the refined liquid sample devoid or having the lower concentration of the interfering component onto the test assay.

13. A method for using a chemical analyzer for removing an interfering component of a liquid sample which may interfere with a test performed on a test assay, the chemical analyzer having a sample cup, a mixing cup, a pipette fitted with a disposable pipette tip and is capable of aspirating and expelling the liquid sample into and from the pipette tip and of dispensing the liquid sample onto the test assay, the method comprising the steps of:
   adding the liquid sample containing the interfering component to the sample cup;
   transferring the liquid sample containing the interfering component from the sample cup to the mixing cup, the mixing cup having an interior space, and a bottom portion and an upper portion situated above the bottom portion, the mixing cup containing a resin containing beads, the resin being lyophilized in a solution of between about two percent (2%) and about ten percent (10%) dextran and between about two percent (2%) and about ten percent (10%) sucrose, or of about two percent (2%) to about fourteen percent (14%) dextran/ sucrose and formed as a physically stable cake which is situated within the interior space of the mixing cup, and wherein the physically stable cake is resuspended in a liquid form when the liquid sample is added to the mixing cup to form a sample/resin solution;
   mixing the sample/resin solution in the mixing cup using the pipette of the chemical analyzer to achieve a mixed sample/resin solution by aspirating the sample/resin solution into the pipette tip and then expelling the sample/resin solution from the pipette tip into the mixing cup, the aspirating and expelling steps being repeated, if or as necessary, to thoroughly mix the sample/resin solution in the mixing cup and achieve the mixed sample/resin solution;
   allowing the mixed sample/resin solution in the mixing cup to rest undisturbed for a predetermined period of time, the predetermined period of time being selected to allow at least a portion of the interfering component of the liquid sample to adhere to the beads of the resin and to allow at least some of the beads to settle in the mixing cup and to occupy the bottom portion thereof, the result of the settling of the beads having the interfering component adhered thereto being the formation of a refined liquid sample devoid or having a lower concentration of the interfering component than the liquid sample and occupying the upper portion of the mixing cup; and
   aspirating into the pipette tip from the mixing cup a predetermined volume of the refined liquid sample occupying the upper portion of the mixing cup for later dispensing of a selected volume of the refined liquid sample devoid or having the lower concentration of the interfering component onto the test assay.

14. The method for removing the interfering component of the liquid sample of claim 13, wherein the predetermined period of time is between about one minute and about fifteen minutes.

15. The method for removing the interfering component of the liquid sample of claim 13, wherein the resin includes at least one of agarose-based beads and silica-based beads.

16. The method for removing the interfering component of the liquid sample of claim 13, wherein the resin is an IMAC (Immobilized Metal Affinity Chromatography) resin.

17. The method for removing the interfering component of the liquid sample of claim 13, wherein the test assay is a bile acid assay; and
   wherein the interfering component of the liquid sample is hemoglobin.

18. The method for removing the interfering component of the liquid sample of claim 13, wherein the interfering component of the liquid sample is a protein.

19. A method using a chemical analyzer for removing an interfering component of a liquid sample which may interfere with a test performed on a test assay, the chemical analyzer having a sample cup, a mixing cup, a pipette fitted with a disposable pipette tip having a discharge end and is capable of aspirating and expelling the liquid sample into and from the pipette tip and of dispensing the liquid sample onto the test assay, the method comprising the steps of:
   adding the liquid sample containing the interfering component to the sample cup;
   transferring the liquid sample containing the interfering component from the sample cup to the mixing cup, the mixing cup containing a resin containing beads, the liquid sample and resin forming a sample/resin solution in the mixing cup;
   mixing the sample/resin solution in the mixing cup using the pipette of the chemical analyzer to achieve a mixed sample/resin solution by aspirating the sample/resin solution into the pipette tip and then expelling the sample/resin solution from the pipette tip into the mixing cup, the aspirating and expelling steps being repeated, if or as necessary, to thoroughly mix the sample/resin solution in the mixing cup and achieve the mixed sample/resin solution;

allowing the mixed sample/resin solution in the mixing cup to rest undisturbed for a first predetermined period of time, the first predetermined period of time being selected to allow at least a portion of the interfering component of the liquid sample to adhere to the beads of the resin and to allow at least some of the beads to settle in the mixing cup and to occupy a bottom portion thereof, the result of the settling of the beads having the interfering component adhered thereto being the formation of a first stage refined liquid sample devoid or having a first lower concentration of the interfering component than the liquid sample and occupying an upper portion of the mixing cup;

aspirating into the pipette tip from the mixing cup a predetermined volume of the first stage refined liquid sample occupying the upper portion of the mixing cup;

allowing the first stage refined liquid sample aspirated into the pipette tip to rest undisturbed for a second predetermined period of time, the second predetermined period of time being selected to allow any remaining interfering component of the liquid sample in the first stage refined liquid sample in the pipette tip to adhere to any beads of the resin remaining in the first stage refined liquid sample in the pipette tip and to allow at least some of the remaining beads to settle in the pipette tip and to form a settled solution occupying a bottom portion of the pipette tip near the discharge end thereof, and wherein the result of the settling of the at least some of the remaining beads having the interfering component adhered thereto and the unattached at least some of the remaining beads being the formation of the settled solution and a second stage, more refined liquid sample devoid or having a second lower concentration of the interfering component than the first stage refined liquid sample and occupying an upper portion of the pipette tip; and expelling from the pipette tip the settled solution occupying the bottom portion of the pipette tip into the mixing cup, leaving the second stage, more refined liquid sample in the pipette tip for later dispensing of a selected volume of the second stage, more refined liquid sample devoid or having the second lower concentration of the interfering component onto the test assay.

20. The method for removing the interfering component of the liquid sample of claim 19, wherein the first predetermined period of time is between about one minute and about fifteen minutes.

21. The method for removing the interfering component of the liquid sample of claim 19, wherein the second predetermined period of time is between about one minute and about fifteen minutes.

22. The method for removing the interfering component of the liquid sample of claim 19, wherein the resin includes at least one of agarose-based beads and silica-based beads.

23. The method for removing the interfering component of the liquid sample of claim 19, wherein the resin is lyophilized in a solution of about two percent (2%) to about fourteen percent (14%) dextran/sucrose.

24. The method for removing the interfering component of the liquid sample of claim 19, wherein the resin is lyophilized in a solution of between about two percent (2%) and about ten percent (10%) dextran and between about two percent (2%) and about ten percent (10%) sucrose.

25. The method for removing the interfering component of the liquid sample of claim 19, wherein the resin is formed as a physically stable cake and resides in the bottom portion of the mixing cup.

26. The method for removing the interfering component of the liquid sample of claim 19, wherein the resin is an IMAC (Immobilized Metal Affinity Chromatography) resin.

27. The method for removing the interfering component of the liquid sample of claim 19, wherein the test assay is a bile acid assay; and
    wherein the interfering component of the liquid sample is hemoglobin.

28. The method for removing the interfering component of the liquid sample of claim 19, wherein the interfering component of the liquid sample is a protein.

29. The mixing cup of claim 7, wherein the resin is an IMAC (Immobilized Metal Affinity Chromatography) resin.

* * * * *